(12) United States Patent
Ishikubo et al.

(10) Patent No.: US 8,673,326 B2
(45) Date of Patent: *Mar. 18, 2014

(54) OIL-IN-WATER EMULSION COMPOSITION AND METHOD FOR PRODUCING THE SAME

(75) Inventors: Akira Ishikubo, Yokohama (JP); Yuji Matsushita, Yokohama (JP); Yosuke Ikebe, Yokohama (JP); Taizo Fujiyama, Yokohama (JP); Tomonori Toyoda, Yokohama (JP); Kazuho Koiwa, Yokohama (JP)

(73) Assignee: Shiseido Company Ltd., Chuo-ku, Tokyo (JP)

( * ) Notice: Subject to any disclaimer, the term of this patent is extended or adjusted under 35 U.S.C. 154(b) by 356 days.

This patent is subject to a terminal disclaimer.

(21) Appl. No.: 12/597,502

(22) PCT Filed: Apr. 25, 2008

(86) PCT No.: PCT/JP2008/058149
§ 371 (c)(1),
(2), (4) Date: Dec. 17, 2009

(87) PCT Pub. No.: WO2008/139908
PCT Pub. Date: Nov. 20, 2008

(65) Prior Publication Data
US 2010/0135938 A1 Jun. 3, 2010

(30) Foreign Application Priority Data
Apr. 26, 2007 (JP) ................. 2007-116809

(51) Int. Cl.
A61K 8/02 (2006.01)
A61K 8/18 (2006.01)
A61K 8/41 (2006.01)
A61K 8/27 (2006.01)
A61Q 1/02 (2006.01)
A61Q 5/06 (2006.01)
A61Q 19/00 (2006.01)

(52) U.S. Cl.
CPC . *A61K 8/416* (2013.01); *A61K 8/27* (2013.01); *A61Q 1/02* (2013.01); *A61Q 5/06* (2013.01); *A61Q 19/00* (2013.01)
USPC ............................. 424/401; 424/59; 424/70.1

(58) Field of Classification Search
None
See application file for complete search history.

(56) References Cited

U.S. PATENT DOCUMENTS

| 5,643,555 A | 7/1997 | Collin et al. |
| 6,017,548 A * | 1/2000 | Epstein et al. ............. 424/401 |
| 6,440,399 B1 | 8/2002 | Gers-Barlag et al. |
| 6,620,407 B1 | 9/2003 | Gers-Barlag et al. |
| 7,186,415 B1 | 3/2007 | Gers-Barlag et al. |
| 2002/0018789 A1 | 2/2002 | Gers-Barlag et al. |
| 2002/0054890 A1* | 5/2002 | Gers-Barlag et al. ......... 424/401 |
| 2002/0127191 A1 | 9/2002 | Gers-Barlag et al. |
| 2003/0017184 A1 | 1/2003 | Gers-Barlag et al. |
| 2004/0018222 A1 | 1/2004 | Gers-Barlag et al. |

FOREIGN PATENT DOCUMENTS

| JP | 8-169808 | 7/1996 |
| JP | 2656226 | 5/1997 |
| JP | 09-263517 | 10/1997 |
| JP | 2000-95638 | 4/2000 |
| JP | 2001-518111 | 10/2001 |
| JP | 2002-522362 | 7/2002 |
| JP | 2002-522363 | 7/2002 |
| JP | 2002-522364 | 7/2002 |
| JP | 2005-154736 | 6/2005 |
| JP | 2006-36763 | 2/2006 |
| JP | 2007-332037 | 12/2007 |

OTHER PUBLICATIONS

Japanese Abstract for Publication No. 2006-036763 published Feb. 9, 2006, 16 pages.
Japanese Abstract for Publication No. 2007-332037 published Dec. 27, 2007, 16 page.
Japanese Abstract for Publication No. 08-169808 published Jul. 2, 1996, eight pages.
International Search Report for corresponding PCT/JP2008/058149 mailed Aug. 26, 2008, 3 pages.
International Preliminary Report on Patentability for corresponding PCT/JP2008/058149 mailed Nov. 19, 2009, 6 pages.
Saleh et al., "Oil-In-Water Emulsions Stabilized by Highly Charged Polyelectrolyte-Grafted Silica Nanoparticles," Langmuir, vol. 21, No. 22, 2005, pp. 9873-9878.
Aveyard et al., "Emulsions Stabilised Solely by Colloidal Particles", Advances in Colloid and Interface Science 100-102 (2003) pp. 503-546.
Patent Abstracts of Japan, Publication No. 2005-154736, 24 pages.
Patent Abstracts of Japan, Publication No. 09-263517, 8 pages.

* cited by examiner

*Primary Examiner* — Brian Gulledge
(74) *Attorney, Agent, or Firm* — Rankin, Hill & Clark LLP

(57) ABSTRACT

The present invention provides an oil-in-water emulsion composition having excellent emulsion stability, low sticky feeling, and low skin irritation. The oil-in-water emulsion composition according to the present invention comprising (a) 1 to 20 mass % of a powder component, (b) 0.001 to 0.5 mass % of a cationic surfactant having two alkyl chains with 12 or more and 22 or less carbon atoms, (c) an oil phase component, and (d) a water phase component, having a structure wherein (a) powder particles are adsorbed on the oil droplets dispersed in the water phase.

16 Claims, 2 Drawing Sheets

OIL-IN-WATER EMULSION COMPOSITION AND METHOD FOR PRODUCING THE SAME

RELATED APPLICATIONS

This application claims the priority of Japanese Patent Application No. 2007-116809 filed on Apr. 26, 2007, which is incorporated herein by reference.

FIELD OF THE INVENTION

The present invention relates to an oil-in-water emulsion composition, and in particular, relates to an oil-in-water emulsion composition that is excellent in emulsion stability, and also relates to a method for producing the same.

BACKGROUND OF THE INVENTION

In an oil-in-water emulsion that is used for cosmetics etc., the aqueous component and the oil component are stably mixed by emulsification with an added surfactant.

In recent years, consumers who put more emphasis on safety are increasing. As a result, the demand is increasing for an oil-in-water emulsion in which even a rarely-irritant surfactant, to only very sensitive users, is not contained, or an oil-in-water emulsion with a surfactant content that does not cause irritation.

An emulsion that is prepared, without the use of a surfactant, by allowing powder to adsorb on the interface has been known as a Pickering emulsion. Thus far, numerous research results have been reported concerning the preparation of a Pickering emulsion (e.g. non-patent literature 1). The application has also been proposed in the cosmetic field (patent literatures 1 and 2).

In recent years, a stable oil-in-water emulsion composition has been obtained, with the combined use of a specific cationic surfactant, polyhydric alcohol, and powder, by emulsifying an oil phase containing an amphiphilic lipid such as ceramide (refer to patent literature 3).

Patent Literature 1: Japanese Patent No. 2656226
Patent Literature 2: PCT Japanese Translation Patent. Publication No. 2001-518111
Patent Literature 3: Japanese Unexamined Patent Publication No. 2006-36763
Non-patent Literature 1: B. Binks et. Al, Advances in Colloid and Interface Science 100-102 (2003)

DISCLOSURE OF THE INVENTION

Problem to be Solved by the Invention

However, it has been very difficult to prepare an oil-in-water Pickering emulsion that satisfies the stability, which is essential when an emulsion is applied to cosmetics, against temperature and agitation in various circumstances.

In patent literature 3, an amphiphilic substance is essential, and the system stability is attempted by forming a liquid crystal structure ($\alpha$-gel) with a surfactant; however, stickiness tends to be caused in use. A technology, wherein a trace amount of amphiphilic substance is blended to obtain a Pickering emulsion, has been reported (e.g., Mukul M. Sharma et al., Journal of Colloid and Interface Science 157, 244-253, (1993)). However, it has been difficult to obtain an emulsion that provides a satisfactory stability as a cosmetic. In addition, a new texture-in-use issue, such as a sticky feeling of the formulation due to amphiphilic substance, arises.

The present invention was made in view of the above-described circumstances, and an object of the invention is to provide an oil-in-water emulsion composition having excellent emulsion stability, low sticky feeling, and low skin irritation; and to provide a simple method for producing the same.

Means to Solve the Problem

The present inventors have diligently studied to achieve the above-described object. As a result, the present inventors have found that an oil-in-water emulsion containing powder, an oil phase component, a water phase component, and a specific amount of a cationic surfactant having two alkyl chains of the length within a certain range, and the components being formed into a specific structure, had excellent emulsion stability, no sticky feeling, and low irritation; thus leading to completion of the present invention.

In addition, the present inventors have found that the oil-in-water emulsion composition can easily be obtained by integrating the cationic surfactant treatment of the powder and the production process of emulsion composition without a separate powder treatment in the emulsion production.

That is, the first embodiment of the present invention is an oil-in-water emulsion composition comprising (a) 1 to 20 mass % of a powder component, (b) 0.001 to 0.5 mass % of a cationic surfactant having two alkyl chains with 12 or more and 22 or less carbon atoms, (c) an oil phase component, and (d) a water phase component, having a structure wherein (a) powder particles are adsorbed on the oil droplets dispersed in the water phase.

In addition, the oil-in-water emulsion composition is characterized in that the (b) cationic surfactant is adsorbed on the (a) powder particles.

In addition, in the oil-in-water emulsion composition, it is preferable that the total amount of the (b) cationic surfactant is 0.001 to 0.1 mass %.

In addition, in the oil-in-water emulsion composition, it is preferable that the (b) cationic surfactant is a dimethyl dialkyl ammonium chloride.

In addition, in the oil-in-water emulsion composition, it is preferable that the (d) water phase component comprises one or more selected from the group consisting of succinoglycan, xanthan gum, and acrylamide.

In addition, in the oil-in-water emulsion composition, it is preferable that 0.001 to 0.5 mass % of hydrophilic surfactant is contained in the water phase.

In addition, the production method of the oil-in-water emulsion composition is characterized by comprising the below-described processes (A) and (B).

(A) a process wherein the powder component and the cationic surfactant having two alkyl chains with 12 or more and 22 or less carbon atoms are dispersed in the water phase component, and (B) a process wherein the above-mentioned dispersion and the oil phase component are mixed after process (A).

In addition, the production method of the oil-in-water emulsion composition is characterized by further comprising the below-described process (C).

(C) a process wherein the hydrophilic surfactant is added and mixed after process (B).

The second embodiment of the present invention is an external skin preparation for sunscreen comprising the oil-in-water emulsion composition and a hydrophobized powder dispersed in the (c) oil phase component.

In addition, in the oil-in-water external skin preparation for sunscreen, it is preferable that the hydrophobized powder comprises hydrophobized titanium dioxide fine particles and/or hydrophobized zinc oxide fine particles.

The third embodiment of the present invention is a makeup composition comprising the oil-in-water emulsion composition and a hydrophobized powder dispersed in the (c) oil phase component, and 50 mass % or more of the oil phase component being a silicone oil.

In addition, in the makeup composition, it is preferable that the hydrophobized powder comprises the hydrophobized fine particles of one or more selected from the group consisting of titanium dioxide, red iron oxide, yellow iron oxide, black iron oxide, and aluminum oxide.

In addition, in the makeup composition, it is preferable that one or more acrylic silicones represented by the below-described general formula (I) are contained.

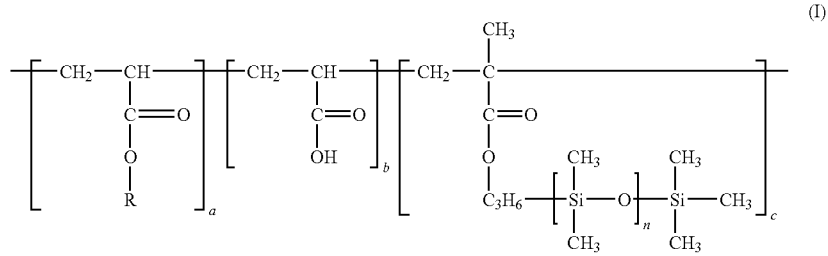

(In the above-described formula, R is an alkyl group having 10 to 20 carbon atoms, a+b+c=1, all a, b, c are 0.2 or higher, and d is an integer of 5 to 100.)

In addition, in the makeup composition, it is preferable that one or more biterminally silicone-modified glycerins represented by the below-described general formula (II) are contained.

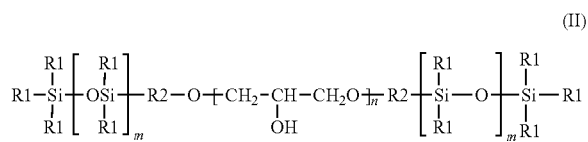

(In the above-described formula, R1 is a linear or branched alkyl group having 1 to 12 carbon atoms or a phenyl group, R2 is an alkylene group having 2 to 11 carbon atoms, m is 10 to 120, and n is 1 to 11.)

The fourth embodiment of the present invention is a hair styling cosmetic comprising the oil-in-water emulsion composition, and the (c) oil phase component in the oil-in-water emulsion composition comprising 1 to 30 mass % of solid oil and 1 to 30 mass % of liquid oil.

In addition, in the hair styling cosmetic, it is preferable that the (a) powder component comprises silica.

Effect of the Invention

According to the present invention, an oil-in-water emulsion composition excellent in emulsion stability can be easily obtained. In addition, a highly functional external skin preparation for sunscreen, makeup composition, and hair styling cosmetic can be obtained by blending the composition.

BEST MODE FOR CARRYING OUT THE INVENTION

Figure 1:
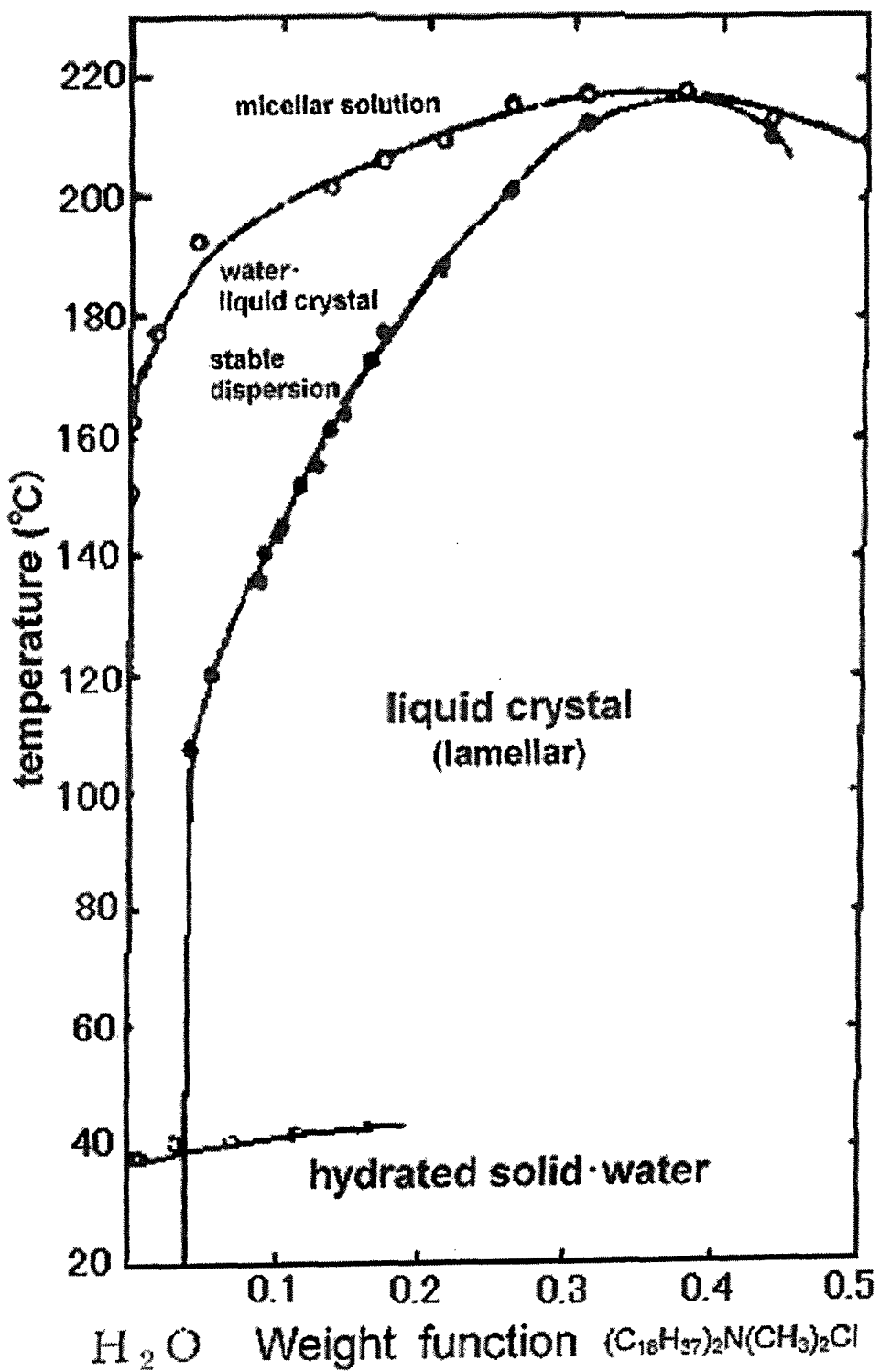
FIG. 1 is a phase diagram of dialkyl methyl ammonium chloride in the two-component system with water.

In the following, the best mode of embodiment of the present invention will be described.

Initially, the oil-in-water emulsion composition, which is the first embodiment of the present invention, will be described.

The oil-in-water emulsion composition of the present invention comprises a specific amount of a cationic surfactant having two alkyl chains of a certain length in addition to an oil phase, water phase, and a powder component, which are components of the conventional Pickering emulsion.

(Two-chain Type Cationic Surfactant)

The alkyl chains of the two-chain type cationic surfactant in the present invention can be either linear or branched, and they don't need to be identical. Examples of the two-chain type cationic surfactant contained in the oil-in-water emulsion of the present invention include dimethyl dilauryl ammonium chloride, diethyl dilauryl ammonium chloride, dipropyl dilauryl ammonium chloride, dimethyl dipalmityl ammonium chloride, diethyl dipalmityl ammonium chloride, dipropyl dipalmityl ammonium chloride, dimethyl dicetyl ammonium chloride, diethyl dicetyl ammonium chloride, dipropyl dicetyl ammonium chloride, dimethyl distearyl ammonium chloride, diethyl distearyl ammonium chloride, dipropyl distearyl ammonium chloride, dimethyl dibehenyl ammonium chloride, diethyl dibehenyl ammonium chloride, dipropyl dibehenyl ammonium chloride, distearoylethyl dimonium chloride, dipalmitoylethyl-dimonium chloride, distearoylethyl hydroxy ethylmonium methosulfate, and dipalmitoylethyl hydroxyethylmonium methosulfate.

In the oil-in-water emulsion composition of the present invention, the chain length of alkyl groups in the two-chain type cationic surfactant is preferably 12 to 22. If the chain length is less than 12, there is a problem in the emulsifying power and emulsion stability. If the chain length exceeds 22, a sticky feeling is increased and there is a problem in usability. The chain length of alkyl groups in the two-chain type cationic surfactant is more preferably 16 to 20. In the oil-in-water emulsion composition of the present invention, dimethyl dialkyl ammonium chloride is especially preferable as the two-chain type cationic surfactant.

In the oil-in-water emulsion composition of the present invention, the blending quantity of the two-chain type cationic surfactant is 0.001 to 0.5 mass % with respect to the total amount of the emulsion, and preferably it is 0.001 to 0.1 mass %. If the blending quantity of the two-chain type cationic surfactant is too much, the composition forms α-gel causing stickiness, and the texture in use tends to decrease.

Normally, the amount of the surfactant in the vicinity of the above-described blending quantity is too small to function as an emulsifier in an emulsion composition. However, in a Pickering emulsion with the structure of the present invention, an excellent emulsion stabilizing ability can be achieved. In addition, the irritation is extremely low.

(Powder Components)

Examples of the powder component contained in the oil-in-water emulsion composition of the present invention include inorganic powders (such as talc, kaolin, mica, sericite, muscovite, phlogopite, synthetic mica, red mica, biotite, vermiculite, magnesium carbonate, calcium carbonate, aluminum silicate, barium silicate, calcium silicate, magnesium silicate, strontium silicate, tungsten acid metal salt, magnesium, silica, zeolite, barium sulfate, calcinated calcium sulfate (calcined gypsum), calcium phosphate, fluorine apatite, hydroxyapatite, and ceramic powder), metal soap (such as zinc myristate, calcium palmitate, aluminium stearate), and boron nitride; organic powders (such as titanium dioxide and zinc oxide); inorganic red series pigments (such as iron titanate); inorganic purple series pigments (such as mangoviolet and cobaltviolet); inorganic green series pigments (such as chromium oxide, chromium hydroxide, and cobalt titanate); inorganic blue series pigments (such as ultramarine and Prussian blue); pearl pigments (such as titanium oxide-coated mica, titanium oxide-coated bismuth oxychloride, titanium oxide-coated talc, colored titanium oxide-coated mica, bismuth oxychloride, and fish scale foil); metal powder pigments (such as aluminum powder and copper powder); organic pigments such as zirconium, barium, or aluminum lake (e.g., organic pigments such as Red No. 201, Red No. 202, Red No. 204, Red No. 205, Red No. 220, Red No. 226, Red No. 228, Red No. 405, Orange No. 203, Orange No. 204, Yellow No. 205, Yellow No. 401 and Blue No. 404, Red No. 3, Red No. 104, Red No. 106, Red No. 227, Red No. 230, Red No. 401, Red No. 505, Orange No. 205, Yellow No. 4, Yellow No. 5, Yellow No. 202, Yellow No. 203, Green No. 3, and Blue No. 1); and natural colorants (such as chlorophyll and β-carotene). One of them can be used alone, or two or more of them can be used in combination. Also, in the present invention, the powder component may be a composite powder which is prepared by coating powder with metal oxide or a modified powder which is prepared by the surface treatment of the powder with compounds.

In the present invention, it is preferable to use silica, titanium dioxide, zinc oxide, or a composite powder thereof. In particular, silica-coated zinc oxide and silica-coated titanium oxide are preferable from the standpoint of affinity of skin, usability, UV-shielding effect, and emulsion stability.

The particle size of the powder is not limited in particular. However, the particle size is preferably 1 to 200 nm from the standpoint of handling easiness and emulsion stability when the powder is blended into cosmetics.

The blending quantity of the powder component in the oil-in-water emulsion of the present invention is preferably 1 to 20 mass % with respect to the total amount of the oil-in-water emulsion composition, and especially preferably 1 to 10 mass %. If the blending quantity is less than 1 mass %, the emulsification may not proceed satisfactorily. If the blending quantity exceeds 20 mass %, the sticky feeling tends to increase.

(Oil Phase Components)

Examples of the oil phase components contained in the oil-in-water emulsion composition of the present invention are listed in the following.

Examples of liquid oil include avocado oil, camellia oil, turtle oil, macadamia nut oil, corn oil, mink oil, olive oil, rapeseed oil, egg oil, sesame oil, persic oil, wheat germ oil, sasanqua oil, castor oil, linseed oil, safflower oil, cottonseed oil, perilla oil, soybean oil, peanut oil, tea seed oil, kaya oil, rice bran oil, paulownia oil, Japanese tung oil, jojoba oil, germ oil, and triglycerin.

Examples of solid oil include cacao butter, coconut oil, horse fat, hardened coconut oil, palm oil, beef tallow, mutton tallow, hardened beef tallow, palm kernel oil, pork tallow, beef bone tallow, Japan wax kernel oil, hardened oil, heatsfoot oil, Japan wax, and hardened castor oil.

Examples of wax include beeswax, candelilla wax, cotton wax, carnauba wax, bayberry wax, Chinese wax, spermaceti wax, montan wax, rice bran wax, lanolin, kapok wax, lanolin acetate, liquid lanolin, sugar cane wax, isopropyl lanolate, hexyl laurate, reduced lanolin, jojoba wax, hard lanolin, shellac wax, POE lanoline alcohol ether, POE lanoline alcohol acetate, POE cholesterol ether, lanolin fatty acid polyethylene glycol, and POE hydrogenated lanolin alcohol ether.

Examples of hydrocarbon oil include liquid paraffin, ozokerite, squalane, pristane, paraffin, ceresin, squalene, petrolatum, and microcrystalline wax.

Examples of higher fatty acid include lauric acid, myristic acid, palmitic acid, stearic acid, behenic acid, oleic acid, undecylenic acid, tolic acid, isostearic acid, linoleic acid, linolenic acid, eicosapentaenoic acid (EPA), and docosahexaenoic acid (DHA).

Examples of higher alcohol include linear alcohol (such as lauryl alcohol, cetyl alcohol, stearyl alcohol, behenyl alcohol, myristyl alcohol, oleyl alcohol, and cetostearyl alcohol); branched-chain alcohol (such as monostearyl glycerin ether (batylalcohol), 2-decyltetradecynol, lanolin alcohol, cholesterol, phytosterol, hexyldodecanol, isostearyl alcohol, and octyldodecanol).

Examples of synthetic ester oil include isopropyl myristate, cetyl octanoate, octyldodecyl myristate, isopropyl palmitate, butyl stearate, hexyl laurate, myristyl myristate, decyl oleate, hexyldecyl dimethyloctanoate, cetyl lactate, myristyl lactate, lanolin acetate, isocetyl stearate, isocetyl isostearate, cholesteryl 12-hydroxystearate, ethylene glycol di-2-ethylhexanoate, dipentaerythritol fatty acid ester, N-alkyl glycol monoisostearate, neopentylglycol dicaprate, diisostearyl malate, glyceryl di-2-heptylundecanoate, trimethylolpropane tri-2-ethylhexanoate, trimethylolpropane triisostearate, pentaerythritol tetra-2-ethylhexanoate, glyceryl tri(2-ethylhexanoate), glyceryl trioctanoate, glyceryl triisopalmitate, trimethylolpropane triisostearate, cetyl 2-ethylhexanoate, 2-ethylhexyl palmitate, glyceryl trimyristate, glyceride tri-2-heptylundecanoate, castor oil fatty acid methyl ester, oleyl oleate, acetoglyceride, 2-heptylundecyl palmitate, diisobutyl adipate, 2-octyldodecyl ester N-lauroyl-L-glutamate, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, and triethyl citrate.

Examples of silicone oil include linear polysiloxanes (such as dimethylpolysiloxane, methylphenylpolysiloxane, and diphenylpolysiloxane); cyclic polysiloxanes (such as octamethylcyclotetrasiloxane, decamethylcyclopentasiloxane, and dodecamethylcyclohexasiloxane); silicon resin forming three-dimensional network structure; silicone rubber; various kinds of modified polysiloxane (such as amino modified polysiloxane, polyether-modified polysiloxane, alkyl-modified polysiloxane, and fluorine-modified polysiloxane); and acrylic silicones.

(Water Phase Components)

In the present invention, water phase include, besides water, lower alcohol, polyhydric alcohol, and so on.

Examples of lower alcohol include ethanol, propanol, isopropanol, isobutyl alcohol, and t-butyl alcohol.

Examples of polyhydric alcohol include dihydric alcohols (such as ethylene glycol, propylene glycol, trimethylene glycol, 1,2-butylene glycol, 1,3-butylene glycol, tetramethylene glycol, 2,3-butylene glycol, pentamethylene glycol, 2-butene-1,4-diol, hexylene glycol, and octylene glycol); trihydric alcohols (such as glycerin and trimethylolpropane); tetrahydric alcohols (such as pentaerythritol, for example, 1,2,6-hexanetriol); pentahydric alcohols (such as xylitol); hexahydric alcohols (such as sorbitol and mannitol); polyhydric alcohol polymers (such as diethylene glycol, dipropylene glycol, triethylene glycol, polypropylene glycol, tetraethylene glycol, diglycerin, polyethylene glycol, triglycerin, tetraglycerin, and polyglycerin); dihydric alcohol alkyl ethers (such as ethylene glycol monomethyl ether, ethylene glycol monoethyl ether, ethylene glycol monobutyl ether, ethylene glycol monophenyl ether, ethylene glycol monohexyl ether, ethylene glycol mono-2-methylhexyl ether, ethylene glycol isoamyl ether, ethylene glycol benzyl ether, ethylene glycol isopropyl ether, ethylene glycol dimethyl ether, ethylene glycol diethyl ether, and ethylene glycol dibutyl ether); dihydric alcohol alkyl ethers (such as diethylene glycol monomethyl ether, diethylene glycol monoethyl ether, diethylene glycol monobutyl ether, diethylene glycol dimethyl ether, diethylene glycol diethyl ether, diethylene glycol butyl ether, diethylene glycol methyl ethyl ether, triethylene glycol monomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ethyl ether, and dipropylene glycol butyl ether); dihydric alcohol ether esters (such as ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disuccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate, and propylene glycol monophenyl ether acetate); glycerol monoalkyl ethers (such as chimyl alcohol, selachyl alcohol, and batyl alcohol); sugar alcohols (such as sorbitol, maltitol, maltotriose, mannitol, sucrose, erythritol, glucose, fructose, starch-degraded sugars, maltose, xylitose, and reduction alcohols of starch-degraded sugars); glysolid; tetrahydrofurfuryl alcohol; POE-tetrahydrofurfuryl alcohol; POP-butyl ether; POP/POE-butyl ether; tripolyoxypropylene glycerin ether; POP-glycerol ether; POP-glycerin ether phosphate; POP/POE-pentaerythritol ether; and polyglycerol.

In the oil-in-water emulsion composition of the present invention, in order to provide the stability against the settling or creaming, over time, of emulsified oil droplets and the stability against powder aggregation, it is preferable to blend a thickener with salt tolerance, in particular succinoglycan, xanthan gum, or acrylamide. When a normal thickener is used, salts that gradually leach from the hydrophobized powder to the water phase act on the thickener and the viscosity may be lowered. However, when a thickener excellent in salt tolerance, such as succinoglycan, is used, the effect due to leached salts is absent. Thus, the settling of emulsified particles can be prevented over a long period of time.

The preferable blending quantity of the thickener is 0.01 to 5 mass % with respect to the total amount of the external skin preparation.

The oil-in-water emulsion composition of the present invention comprises the above-described components and forms a so-called Pickering emulsion.

A Pickering emulsion is known to be an O/P/W emulsion wherein the oil phase is uniformly dispersed, in the oil-in-water dispersion system, into the water phase by fine particles (powder). In the present invention, the emulsion stability by powder is enhanced by applying a cationic surfactant with a specific structure to such an emulsion.

In the following, the structure of the oil-in-water emulsion composition of the present invention is explained along with the production method.

In the production method of the present invention, prior to the emulsification process, it is necessary to allow a cationic surfactant having two alkyl chains with 12 or more and 22 or less carbon atoms to be a water dispersion with a lamellar liquid crystal structure. Similarly, the powder component is also uniformly dispersed in water before emulsification.

In a specific method, for example, a powder component and a cationic surfactant are added to water, and a uniform water dispersion containing a lamellar structure and powder can be formed with a homomixer or by ultrasonic wave treatment etc. Also, a powder component and a cationic surfactant may be separately dissolved in respective portions of water, dispersed, and then mixed together. In these processes, other water phase components may be added and mixed.

The cationic surfactant having two alkyl chains with 12 or more and 22 or less carbon atoms used in the present invention forms a lamellar liquid crystal structure in water, wherein lipophilic groups are associated in wide concentration and temperature ranges. For example, dialkyl methyl lammonium chloride in the two-component system with water is known to take a liquid crystal structure, as shown in FIG. 1, at a low concentration. In the present invention, in particular, it is desirable that the cationic surfactant is in the state that corresponds to the water/liquid crystal stable dispersion in FIG. 1, namely, the state in which small lamellar structures of the cationic surfactant are dispersed in water.

If the above-described cationic surfactant in a lamellar liquid-crystalline state is dispersed in the same water system as that of the powder component, positively charged liquid-crystalline hydrophilic groups adsorb on the normally negatively charged powder particle surface. If this is dispersed by a suitable treatment, a dispersion of the powder particles, on the surface of which countless liquid-crystalline surfactants are adsorbed, is considered to be formed.

Figure 2:
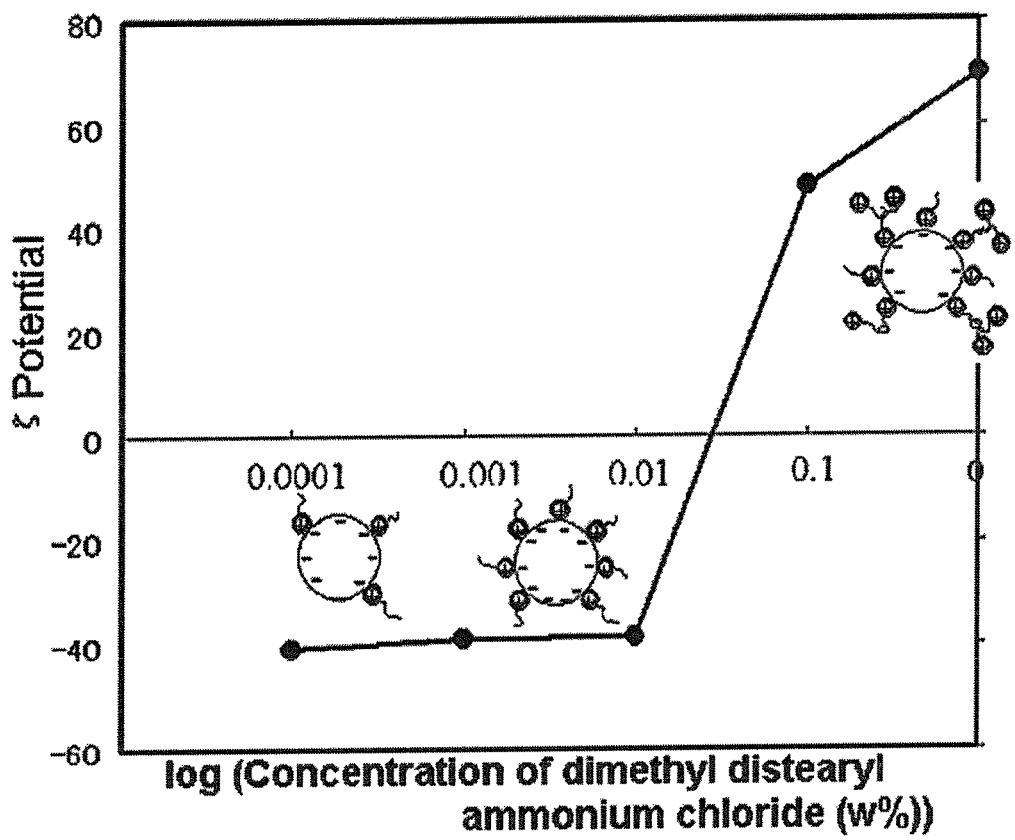
FIG. 2 is a graph that shows the measured ζ-potential results for the silica-coated titanium oxide powder, which was dispersed in water with dimethyl distearyl ammonium chloride, in the production of an oil-in-water emulsion composition, wherein the blending quantity of dimethyl distearyl ammonium chloride was varied, silica-coated titanium oxide: 3 weight %, oil component: 47 weight %, and water: balance.

FIG. 2 shows the measured $\zeta$-potential results for the silica-coated titanium oxide powder, which was dispersed in water with dimethyl distearyl ammonium chloride, in the production of an oil-in-water emulsion composition, wherein the blending quantity of dimethyl distearyl ammonium chloride was varied, silica-coated titanium oxide: 3 weight %, oil component: 47 weight %, and water: balance. As seen in FIG. 2, the $\zeta$-potential, which is the surface potential of powder, shifts to the positive direction with an increase in the cationic surfactant concentration. Thus, it is presumed that dimethyl distearyl ammonium chloride having a cationic group is adsorbed on the powder surface. From FIG. 2, it is clear that the adsorbed amount increases with an increase in the blended cationic surfactant against powder. However, if the blending quantity is too high, the inversion to the water-in-oil may take place during emulsification. Accordingly, in the present invention, the blending ratio of a specific cationic surfactant to the powder component is preferably in the vicinity of 5:0.001 to 5:1 though it depends upon other formulation components.

After the above-described process, the oil-in-water emulsion composition of the present invention can be obtained by adding an oil phase component to the dispersion of the obtained powder particles, on which a cationic surfactant is adsorbed, and by emulsifying with an emulsifying machine etc. The addition of the oil phase component may be carried out under heating as necessary. Depending upon the state of the oil phase component, a treatment such as fragmentation may be carried out beforehand.

Thus, the present invention can be thought to be an O/P/W emulsion, wherein an oil phase is uniformly dispersed into the water phase with the help of fine particles on which a specific cationic surfactant is adsorbed.

Here, it is considered that the added oil component enters into the association sites of lipophilic groups of a lamellar liquid crystal that is adsorbed on the powder, and the oil droplets, on which powder particles are adsorbed, are formed at the interface with the water phase. On this occasion, the powder adsorption on the oil droplets is enhanced by the action of the specific cationic surfactant. Thus, a composition more excellent in emulsion stability than the conventional O/P/W emulsion, wherein oil droplets are dispersed only by the adsorption power of the powder, is presumably obtained.

Thus, it is considered, in the emulsion composition of the present invention, that the powder particles are adsorbed on the oil droplets that are dispersed in the water phase, and a structure, wherein a cationic surfactant is adsorbed on the powder particles, is formed.

In the production method of the oil-in-water emulsion composition of the present invention, it is preferable as described above that a specific cationic surfactant of a liquid crystalline state is adsorbed on the powder before the emulsification of the water phase and the oil phase. A satisfactory improvement in the emulsion state and emulsion stability cannot be achieved by the addition of the cationic surfactant during or after emulsification.

(Other Components)

In the oil-in-water emulsion composition according to the present invention, hydrophilic surfactant and/or lipophilic surfactant may be blended so far as the aforementioned Pickering emulsion is not deteriorated. The hydrophilic surfactant contributes to improvement of affinity of skin by eliminating frictional feeling owing to emulsification with powder. The lipophilic surfactant contributes to improvement of emulsion stability over time.

When the hydrophilic surfactant is blended, it is preferable that an O/P/W emulsion is formed from the aforementioned essential components, and then the hydrophilic surfactant is added and mixed to the external aqueous phase of the emulsion. The blending quantity of the added hydrophilic surfactant is preferably 0.001 to 0.5 mass % with respect to the composition. By adding small quantity of hydrophilic surfactant after the emulsification process, it is possible to eliminate the frictional feeling caused by the emulsion without allowing the surfactant to affect the structure of the O/P/W emulsion.

Examples of the hydrophilic surfactant which can be blended include glycerol or polyglycerol fatty acid esters, propylene glycol fatty acid esters, POE sorbitan fatty acid esters, POE sorbitol fatty acid esters, POE glycerol fatty acid esters, POE fatty acid esters, POE alkyl ethers, POE alkylphenyl ethers, POE/POP alkyl ethers, POE castor oil or POE hardened castor oil derivatives, POE beeswax/lanolin derivatives, alkanolamides, POE propylene glycol fatty acid esters, POE alkylamine, POE fatty acid amide, polyoxyethylene alkylether sulfate, and alkyl amido amine. One of these hydrophilic surfactants can be blended alone, or two or more of them can be blended in combination.

The lipophilic surfactant can be added as an oil phase component during the preparation of an O/P/W emulsion. When the lipophilic surfactant is blended, its blending quantity is in a range that the lipophilic surfactant does not act as emulsifier, namely, about 0.01 to 5 mass % with respect to the composition. As mentioned above, the structure of the O/P/W emulsion according to the present invention is that highly-stable oil droplets, of which powder particles are absorbed on the surface through the surfactants, can be formed by emulsifying with powders of which lamella liquid crystals of a specific cationic surfactant are absorbed on the surface in advance. Thus, even if a small amount of lipophilic surfactant which is dissolved in an oil is added as an oil phase component, it does not affect on the powder emulsification, and the lipophilic surfactant itself hardly contribute to the emulsification. On the other hand, an emulsion having excellent stability over time can be obtained by dissolving the lipophilic surfactant in emulsified oil droplets (oil phase).

Examples of the lipophilic surfactant which can be blended include sorbitan fatty acid esters such as sorbitan monooleate, sorbitan monoisostearate, sorbitan monopalmitate, sorbitan sesquioleate, sorbitan trioleate, and diglycerol sorbitan penta-2 ethylhexylate, glycerins such as glyceryl monoerucate, glyceryl sesquioleate, glyceryl monostearate, diglyceryl monostearate, and mono-stearic acid glycerine malic acid, or polyglycerin fatty acids, lipophilic sucrose fatty acid esters such as sucrose polyerucate, sucrose polyoleate, and sucrose polyisostearate, propylene glycol fatty acid esters such as propylene glycol monostearate, hardened castor oil derivatives, glycerin alkyl ethers, polyether-modified silicones, aliphatic alcohols such as cetyl alcohol, stearyl alcohol, and behenyl alcohol. One of these lipophilic surfactants can be blended alone, or two or more of them can be blended in combination.

In the oil-in-water emulsion composition of the present invention, the components normally used in cosmetics and quasi-drugs can be blended in addition to the above-described components so far as the effect of the present invention is not undermined, and the production can be carried out according to the normal method. There is no limitation in the components which can be blended, and examples of other components include moisturizers, monosaccharides, oligosaccharides, organic amines, UV absorbers, antioxidants, antiseptics (such as ethyl paraben and butyl paraben), whitening agents (such as saxifraga sarmentosa extract, arbutins, tranexamic acids, and potassium 4-methoxysalicylate), various extracts (such as Zingiber officinale, phellodendron bark, goldthread, lithospermum root, birch, loquat, carrot, aloe, malva sylvestris (mallow), iris, vitis vinifera (grape), luffa cylindrica, lily, saffron, cnidium officinale, ginger, hypericum perforatum, ononis spinosa, allium sativum (gerlic), capsicum frutescens, citrus unshiu peel, angelica acutiloba, paeonia suffruticosa extract, and sea alga), activator agents (such as panthenyl ethyl ether, nicotinamide, biotin, pantothenic acid, royal jelly, and cholesterol derivatives), antiseborrheic agents (such as pyridoxines and thianthol), perfume, and colorant.

Examples of moisturizer include chondroitin sulfate, hyaluronic acid, mucoitin sulfate, charonin acid, atelocollagen, cholesteryl 12-hydroxystearate, sodium lactate, bile acid salts, dl-pyrrolidonecarboxylic acid salts, short-chain soluble collagen, diglycerol (EO) PO adducts, chestnut rose (R. roxburghii plena) extract, yarrow (Achillea millefolium) extract, and melilot extract in addition to the aforementioned polyhydric alcohols.

Examples of monosaccharide include trioses (such as D-glycerylaldehyde and dihydroxyacetone); tetroses (such as D-erythrose, D-erythrulose, D-threose, and erythritol); pentoses (such as L-arabinose, D-xylose, L-lyxose, D-arabinose, D-ribose, D-riburose, D-xylulose, and L-xylulose); hexoses (such as D-glucose, D-talose, D-psicose, D-galactose, D-fructose, L-galactose, L-mannose, and D-tagatose); heptoses (such as aldoheptose and heptulose); octoses (such as octulose); deoxysugars (such as 2-deoxy-D-ribose, 6-deoxy-L-galactose, and 6-deoxy-L-mannose); amino sugars (such as D-glucosamine, D-galactosamine, sialic acid, aminouronic acid, and muramic acid); and uronic acids (such as D-glucuronic acid, D-mannuronic acid, L-guluronic acid, D-galacturonic acid, and L-iduronic acid).

Examples of oligosaccharide include sucrose, gentianose, umbelliferose, lactose, planteose, isolychnoses, α,α-trehalose, raffinose, lychnoses, umbilicin, and stachyose verbascoses.

Examples of amino acid include neutral amino acids (such as threonine and cysteine); basic amino acids (such as hydroxylysine). Examples of amino acid derivative include sodium acylsarcosinate (sodium lauroylsarcosinate), acyl-glutamic acid salt, sodium acyl-β-alanine, glutathione, and pyrrolidonecarboxylic acid.

Examples of organic amine include monoethanolamine, diethanolamine, triethanolamine, morpholine, triisopropanolamine, 2-amino-2-methyl-1,3-propanediol, and 2-amino-2-methyl-1-propanol.

As UV protection agent, examples of organic UV absorber include benzoic acid UV absorbers (such as p-aminobenzoic acid (hereinafter abbreviated as "PABA"), PABA monoglycerin ester, N,N-dipropoxy PABA ethyl ester, N,N-diethoxy PABA ethyl ester, N,N-dimethyl PABA butyl ester, and N,N-dimethyl PABA ethyl ester); anthranilic acid UV absorbers (such as homomethyl-N-acetyl anthranilate); salicylic acid UV absorbers (such as amyl salicylate, menthyl salicylate, homomenthyl salicylate, octyl salicylate, phenyl salicylate, benzyl salicylate, and p-isopropanol phenyl salicylate); cinnamic acid UV absorbers (such as octyl cinnamate, ethyl-4-isopropylcinnamate, methyl-2,5-diisopropylcinnamate, ethyl-2,4-diisopropylcinnamate, methyl-2,4-diisopropylcinnamate, propyl-p-methoxycinnamate, isopropyl-p-methoxycinnamate, isoamyl-p-methoxycinnamate, octyl-p-methoxycinnamate (2-ethylhexyl-p-methoxycinnamate), 2-ethoxyethyl-p-methoxycinnamate, cyclohexyl-p-methoxycinnamate, ethyl-α-cyano-β-phenylcinnamate, 2-ethylhexyl-α-cyano-β-phenylcinnamate, and glyceryl mono-2-ethyl hexanoyl-diparamethoxycinnamate); benzophenone UV absorbers (such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl-4'-phenyl-benzophenone-2-carboxylate, 2-hydroxy-4-n-octoxybenzophenone, and 4-hydroxy-3-carboxybenzophenone); 3-(4'-methylbenzylidene)-d,1-camphor, 3-benzylidene-d,1-camphor; 2-phenyl-5-methyl benzoxazole; 2-(2-hydroxy-5-methylphenyl benzotriazole; 2-(2'-hydroxy-5'-t-octylphenyl)benzotriazole; 2-(2'-hydroxy-5'-methylphenyl)benzotriazole; dibenzaladine; dianisoylmethane; 4-methoxy-4'-t-butyldibenzoylmethane; and 5-(3,3-dimethyl-2-norbornylidene)-3-pentane-2-one.

Examples of inorganic UV absorber which is inorganic compound include titanium oxide, zinc oxide, iron oxide, cerium oxide, or composite powder containing thereof.

Examples of antioxidant aid include phosphoric acid, citric acid, ascorbic acid, maleic acid, malonic acid, succinic acid, fumaric acid, cephalin, hexametaphosphates, phytic acid, and ethylenediaminetetraacetic acid.

The formulation of the oil-in-water emulsion composition of the present invention is not specified, and the formulation can be suitably selected depending upon the formulation components and the intended use, for example, lotion, milky lotion, cream, or gel.

In the following, the external skin preparation for sunscreen, which is the second embodiment of the present invention, will be explained.

Generally, for a UV light protection external skin preparation, an oily organic UV protection agent and a powderly inorganic UV protection agent are blended in the base. From the standpoint that these UV protection agents are blended in large amounts, a water-in-oil emulsion composition is widely used as the base. An external skin preparation of such a configuration has an unpleasant oily feeling, and a powdery feeling is also strong; thus good texture in use may not be achieved.

On the other hand, if an oil-in-water emulsion composition is used as the base, an external skin preparation with a refreshing feeling and light feeling can be obtained because of the composition characteristics. However, it is difficult to maintain the emulsion stability when a sufficient amount of the above-described UV protection agents are blended into the oil-in-water emulsion. In addition, there are issues in that the conventional oil-in-water external skin preparation for sunscreen is inferior, in water resistance, to that of the water-in-oil and it tends to be removed by sweat and sebum.

Thus, the present inventors further investigated the properties of the oil-in-water emulsion composition of the present invention and found that an oil-in-water external skin preparation for sunscreen that is excellent in the emulsion stability and low in the frictional feeling could be obtained by blending the above composition.

The components in the oil-in-water emulsion composition, which is blended in the external skin preparation for sunscreen of the present invention, are as described above. However, the external skin preparation for sunscreen of the present invention is prepared by dispersing a hydrophobized powder in the oil phase component in the oil-in-water emulsion composition.

Examples of hydrophobized powder to be dispersed in the oil phase component include a hydrophobized powder which is prepared by hydrophobizing the surface of inorganic powder particle in a wet method using solvent, a gas phase method, or a mechanochemical method with silicones such as methylhydrogenpolysiloxane and dimethylpolysiloxane; dextrin fatty acid ester; higher fatty acid; higher alcohol; fatty acid ester; metallic soap; alkyl phosphate ether; fluorine compound; or hydrocarbons such as squalane and paraffin; or a hydrophobized powder which is prepared by coating inorganic powder particle with silica and then hydrophobizing it with alkyl-modified silane coupling agent and so on.

Examples of the inorganic powder particle which is hydrophobized as mentioned above, include titanium oxide, zinc oxide, talc, mica, sericite, kaolin, titanated mica, black iron oxide, yellow iron oxide, red iron oxide, ultramarine, Prussian blue, chromium oxide, and chromium hydroxide. In the present invention, particularly hydrophobized fine titanium dioxide and/or hydrophobized fine zinc oxide is preferably contained.

When considering the characteristics of the present invention that the hydrophobized powder is dispersed in the oil phase component, it is preferable that the average particle size is smaller than the size of oil phase emulsified particles. In particular, when considering that the hydrophobized powder is used as a UV scattering agent in the external skin preparation for sunscreen of the present invention, it is preferable to use the powder with the average particle size of 100 nm or less.

The external skin preparation for sunscreen of the present invention can be produced, with the use of the above-described essential components and other optional components so far as the effect is not undermined, according to the above-described production method of the oil-in-water emulsion composition of the present invention. For example, the desired external skin preparation for sunscreen can be obtained by adding a powder component and a specific cationic surfactant to a portion of water, mixing them under heating, adding and mixing the rest of water and water phase components, and adding and mixing, under heating, the oil phase component which has been beforehand dissolved by heating and dispersed hydrophobic powder by stirring.

In addition, the formulation can be suitably selected depending upon the formulation components and the intended use, for example, lotion, milky lotion, cream, or gel.

The third embodiment of the present invention is a makeup composition.

In the past, various powders have been blended in makeup cosmetics to provide the functions such as coloring of skin and hair, concealment of pigmented spots, freckles, etc., skin protection against UV light, and the absorption of sweat and sebum. For the emulsion composition wherein such powder is blended, the technology that can prevent the coalescence of emulsified particles and the aggregation/precipitation of fine powder particles, they are due to the passage of time or the change of temperature, and can also provide satisfactory powder dispersion stability is sought-after.

The oil-in-water emulsion composition provides a fresh and light feeling in use; thus it is preferred for cosmetics such as milky lotion, cream, and emulsion-type foundation. For the provision of such a desirable feeling in use and high water repellency, silicone oil is widely used. However, in the case of the oil solution with a high rate of silicone oil, which has low compatibility with other oil components such as hydrocarbons, some ingenuity was necessary in the selection of the best surfactant, and it was difficult to stably emulsify the oil solution. In particular, when a silicone surfactant is used for the emulsification of silicone oil, a large blending quantity was necessary for stabilization, and there was an issue in that a sticky feeling is generated for the composition because of the surfactant.

Thus, the present inventors further investigated the properties of the above-described oil-in-water emulsion composition of the present invention. As a result, the present inventors found that an oil-in-water makeup composition excellent in emulsion stability and with a low sticky feeling could be obtained by blending the composition of the invention.

The components in the oil-in-water emulsion composition, which is blended in the makeup composition of the present invention, are as described above. However, the makeup composition of the present invention is prepared by dispersing a hydrophobized powder into the oil phase component in the oil-in-water emulsion composition.

Examples of hydrophobized powder to be dispersed in the oil phase components include a hydrophobized powder which is prepared by hydrophobizing the surface of inorganic powder particle in a wet method using solvent, a gas phase method, or a mechanochemical method with silicones such as methylhydrogenpolysiloxane and dimethylpolysiloxane; dextrin fatty acid ester; higher fatty acid; higher alcohol; fatty acid ester; metallic soap; alkyl phosphate ether; fluorine compound; or hydrocarbons such as squalane or paraffin; or a hydrophobized powder which is prepared by coating inorganic powder particle with silica and then hydrophobizing it with alkyl-modified silane coupling agent and so on.

Examples of the inorganic powder particle which is hydrophobized as mentioned above, include titanium oxide, zinc oxide, talc, mica, sericite, kaolin, titanated mica, black iron oxide, yellow iron oxide, red iron oxide, ultramarine, Prussian blue, chromium oxide, and chromium hydroxide. In the present invention, particularly hydrophobized fine titanium dioxide, red iron oxide, yellow iron oxide, black iron oxide and/or aluminum oxide is preferably contained. Such a hydrophobized powder has high water resistance against sebum, sweat, etc. and is long-lasting. Therefore, a composition with a good feeling upon application and excellent characteristics after application can be obtained by dispersing the hydrophobized powder into the oil phase component in the oil-in-water emulsion composition.

When considering the characteristics of the present invention in that the hydrophobized powder is dispersed in the oil phase component, it is preferable that the average particle size is smaller than the size of oil phase emulsified particles. In particular, in the makeup composition of the present invention, it is preferable to use the powder with an average particle size of 100 nm or less.

In addition, the makeup composition of the present invention contains 50 mass % or more silicone oil, with respect to the oil phase component, in the oil-in-water emulsion composition, which is the essential component.

Examples of silicone oil which can be applied in the present invention include linear polysiloxanes (such as dimethylpolysiloxane, methylphenylpolysiloxane, and diphenylpolysiloxane); cyclic polysiloxanes (such as octamethylcyclotetrasiloxane, decamethylcyclopentasiloxane, and dodecamethylcyclohexasiloxane); silicon resin forming three-dimensional network structure; silicone rubber; various kinds of modified polysiloxane (such as amino-modified polysiloxane, polyether-modified polysiloxane, alkyl-modified polysiloxane, and fluorine-modified polysiloxane), and acrylic silicones. One of these silicone oils can be blended alone, or two or more of them can be blended in combination.

In particular, in the present invention, it is preferable to use an acrylic silicone represented by the below-described general formula (I).

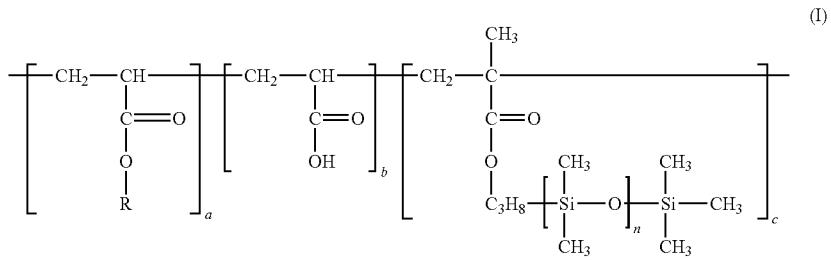

(I)

In the above-described general formula (I), R is an alkyl group having 10 to 20 carbon atoms. In addition, a+b+c=1, all a, b, c are 0.2 or higher, and d is an integer of 5 to 100.

In the present invention, it is also preferable that a biterminally silicone-modified glycerin represented by the below-described general formula (II) is blended.

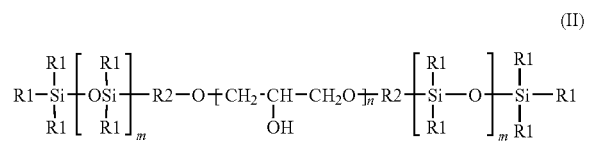

(II)

In the above-described formula, R1 is a linear or branched alkyl group having 1 to 12 carbon atoms or a phenyl group, and R2 is an alkylene group having 2 to 11 carbon atoms. In addition, m is 10 to 120 and n is 1 to 11.

The silicone oils represented by the above-described general formulas (I) and (II) can be blended alone or in combination.

In the oil phase in the oil-in-water emulsion composition contained in the makeup composition of the present invention, oils usually used in cosmetics, such as liquid oil, waxes, hydrocarbon oil, higher fatty acid, higher alcohol, and synthetic ester oil, may be blended in addition to a specific amount of silicone oil.

In the makeup composition of the present invention, other components can be suitably blended so far as the effect of the present invention is not undermined, in addition to the above-described essential components. The makeup composition of the present invention can be produced according to the above-described production method of the oil-in-water emulsion composition of the present invention. For example, the desired makeup composition can be obtained by adding a powder component and a specific cationic surfactant to a portion of water, mixing them under heating, adding and mixing the rest of water and water phase components, and adding and mixing, under heating, the oil phase component which has been beforehand dissolved by heating and dispersed the hydrophobic powder by stirring.

In addition, the formulation can be suitably selected depending upon the formulation components and the intended use, for example, lotion, milky lotion, cream, or gel.

The fourth embodiment of the present invention is a hair styling cosmetic.

In the past, for the styling preparation used for hair, not only the hair styling ability but also non-sticky feeling during use and high moisture resistance have been sought-after. As a general means for increasing the hair styling ability and moisture resistance, for example, the increasing of the product viscosity by the adjustment of the amount of solid oil can be considered. Although the hair styling ability can be improved by this, the sticky feeling often increased at the same time.

On the other hand, it is known that the stickiness can be remedied by using an oil-in-water emulsion in the hair styling preparation. However, it was difficult to achieve the oil selection for optimum hair styling ability and to achieve stable emulsification at the same time.

Thus, the present inventors further investigated the properties of the above-described oil-in-water emulsion composition of the present invention. As a result, the present inventors found that a hair styling cosmetic excellent in emulsion stability, hair styling power, and moisture resistance, and with a low sticky feeling could be obtained by blending the composition of the invention.

The components in the oil-in-water emulsion composition, which is blended in the hair styling cosmetic of the present invention, are as described above. However, the present invention comprises 1 to 30 mass % of solid oil and 1 to 30 mass % of liquid oil with respect to the total components that constitute the present invention.

In the present invention, the solid oil indicates solid oil (at room temperature) components generally used in cosmetics. Examples of such an oil include solid oils such as cacao butter, coconut oil, horse fat, hardened coconut oil, palm oil, beef tallow, mutton tallow, hardened beef tallow, palm kernel oil, pork tallow, beef bone tallow, Japan wax kernel oil, hardened oil, heatsfoot oil, Japan wax, and hardened castor oil; waxes such as beeswax, candelilla wax, cotton wax, carnauba wax, bayberry wax, Chinese wax, spermaceti wax, montan wax, rice bran wax, lanolin, kapok wax, lanolin acetate, sugar cane wax, isopropyl lanolate, hexyl laurate, reduced lanolin, jojoba wax, hard lanolin, shellac wax, POE lanoline alcohol ether, POE lanoline alcohol acetate, POE cholesterol ether, and POE hydrogenated lanolin alcohol ether; hydrocarbon waxes such as polyethylene wax, paraffin wax, ceresin, petrolatum, microcrystalline wax, lunacera, and ozokerite; higher alcohols such as cetyl alcohol, cetostearyl alcohol, stearyl alcohol, and behenyl alcohol; fatty acid glycerol ethers such as monostearylglycerin ether (batylalcohol); and fatty acid glyceride such as acetoglyceride and glyceride tri-2-heptylundecanoate. One of these oils can be used alone or two or more of them can be used in combination.

The blending quantity of the solid oil in the hair styling cosmetic of the present invention is preferably 1 to 30 mass % of the total components, and more preferably 2 to 15 mass %. If the blending quantity of the solid oil is less than 1 mass %, the hair styling power may not be satisfactory. If the blending quantity exceeds 30 mass %, the stickiness may be caused.

The liquid oil used in the present invention indicates liquid oil (at room temperature) components generally used in cosmetics. Examples of such an oil include liquid oils such as avocado oil, evening primrose oil, camellia oil, turtle oil, macadamia nut oil, sunflower oil, almond oil, corn oil, mink oil, olive oil, rapeseed oil, egg oil, sesame oil, persic oil, wheat germ oil, sasanqua oil, castor oil, linseed oil, safflower oil, cottonseed oil, perilla oil, soybean oil, peanut oil, tea seed oil, kaya oil, rice bran oil, paulownia oil, Japanese tung oil, jojoba oil, and germ oil; ester oils such as cetyl octanoate, cetyl 2-ethylhexanoate, hexyldecyl dimethyloctanoate, ethyl laurate, hexyl laurate, isopropyl myristate, 2-hexyldecyl myristate, myristyl myristate, octyldodecyl myristate, isopropyl palmitate, 2-ethylhexyl palmitate, 2-hexyldecyl palmitate, 2-heptylundecyl palmitate, butyl stearate, isocetyl stearate, isocetyl isostearate, decyl oleate, dodecyl oleate, oleyl oleate, myristyl lactate, cetyl lactate, diisostearyl malate, cholesteryl 12-hydroxystearate, castor oil fatty acid methyl ester, N-lauroyl-L-glutamate 2-octyldodecyl ester, 2-ethylhexyl succinate, diisobutyl adipate, 2-hexyldecyl adipate, di-2-heptylundecyl adipate, diisopropyl sebacate, di-2-ethylhexyl sebacate, ethyleneglycol di-2-ethylhexanoate, neopentylglycol dicaprate, neopentylglycol dioctanoate, acetoglyceride, glyceryl di-2-heptylundecanoate, glyceryl trioctanoate, glyceryl tri(2-ethylhexanoate), glyceryl trimyristate, glyceryl triisopalmitate, glyceride tri-2-heptylundecanoate, trimethylolpropane tri-2-ethylhexanoate, trimethylolpropane triisostearate, pentaerythritol tetraoctanoate, and pentaerythritol tetra-2-ethylhexanoate; hydrocarbon oils such as liquid paraffin, ozocerite, squalene, pristane, and polybutene; and silicone oils such as liner polysiloxanes (e.g., dimethylpolysiloxane, methylphenyl polysiloxane, and diphenyl polysiloxane), cyclic polysiloxanes (e.g. octamethylcyclotetrasiloxane, decamethylcyclopentasiloxane, and dodecamethylcyclohexasiloxane), and various kinds of modified polysiloxanes (e.g., amino-modified polysiloxane, polyether-modified polysiloxane, alkyl-modified polysiloxane, and fluorine-modified polysiloxane). One of these oils can be used alone or two or more of them can be used in combination.

The blending quantity of the liquid oil in the hair styling cosmetic of the present invention is preferably 1 to 30 mass % with respect to the total components, and more preferably 5 to 20 mass %. If the blending quantity of the liquid oil is less than 1 mass %, the hair styling power may not be satisfactory. If the blending quantity exceeds 30 mass %, the stickiness may be caused.

In the hair styling cosmetic of the present invention, it is preferable to blend silica, titanium dioxide, zinc oxide, or a composite powder thereof as the powder component, which is an essential component in the oil-in-water emulsion composition. In particular, the use of silica is preferable because it has transparency and it does not turn white after application.

The particle size of the powder is not limited in particular. However, the particle size is preferably 1 to 100 nm from the standpoint of handling easiness and emulsion stability when the powder is blended into cosmetics.

The hair styling cosmetic of the present invention can be produced, with the use of the above-described essential components and other optional components so far as the effect is not undermined, according to the above-described production method of the oil-in-water emulsion composition of the present invention. For example, the desired hair styling cosmetic can be obtained by adding a powder component and a specific cationic surfactant to a portion of water, mixing them under heating, adding and mixing the rest of water and water phase components, and adding and mixing, under heating, the oil phase component containing beforehand-dissolved solid oil and liquid oil.

In addition, the formulation can be suitably selected depending upon the formulation components and the intended use, for example, lotion, milky lotion, cream, or gel.

EXAMPLE 1

Hereinafter, the present invention will be more concretely described with reference to examples. However, the technical scope of the present invention should not be limitedly interpreted by these examples. In the examples, "mass %" or "%", which represents the blending quantity, indicates mass % with respect to the total amount of the composition unless otherwise noted.

Initially, the evaluation methods used in the present examples will be explained.

Evaluation (1): Emulsion Stability (Appearance)

The appearance of the emulsion was observed by the naked eye within 1 day of the preparation of the emulsion.

O: The sample was uniform, and the oil floatation or powder aggregation was not observed.

Δ: The sample was nearly uniform; however, some oil floatation was observed.

X: The sample was not uniform, or a significant separation of the oil phase or the powder aggregation was observed.

Evaluation (2): Emulsion Stability (Emulsified Particles)

When the sample was observed with an optical microscope,

O: Emulsified particles were uniform, and the coalescence or aggregation was not observed.

Δ: Emulsified particles were nearly uniform; however, slight coalescence or aggregation was observed.

X: Emulsified particles were not uniform, and significant coalescence or aggregation was observed.

Evaluation (3): Skin Irritation Test

A 24-hour occlusive patch test was performed on the medial side of the upper arm of 10 panelists, and the average value was calculated based on the following criteria.

0 . . . No abnormality was observed.

1 . . . . Slight redness was observed.

2 . . . . Redness was observed.

3 . . . . Redness and papules were observed.

The evaluation criteria for the "skin irritation test" were as follows.

⊚: The average value of 10 panelists was 0 or higher and less than 0.15.

O: The average value of 10 panelists was 0.15 or higher and less than 0.2.

Δ: The average value of 10 panelists was 0.2 or higher and less than 0.3.

X: The average value of 10 panelists was 0.3 or higher.

Evaluation (4): Evaluation of Sticky Feeling Upon Application

The actual usage test of each sample was performed by 10 professional panelists. The evaluation criteria were as follows.

⊚: 8 or more panelists acknowledged that there was no sticky feeling upon application.

O: 6 or more and less than 8 panelists acknowledged that there was no sticky feeling upon application.

Δ: 3 or more and less than 6 panelists acknowledged that there was no sticky feeling upon application.

X: less than 3 panelists acknowledged that there was no sticky feeling upon application.

Oil-in-water emulsions having the blending compositions listed in Table 1 were produced by the below-described method. The above-described evaluation tests (1) to (4) were performed for each sample.

TABLE 1

|  | Test Example | | |
|---|---|---|---|
|  | 1 | 2 | 3 |
| Glycerin | 3.0 | 3.0 | 3.0 |
| Succinoglycan | 0.35 | 0.35 | 0.35 |
| Silica-coated zinc oxide | 3.0 | 3.0 | 3.0 |
| Trimethyl Stearyl ammonium chloride | — | 0.01 | — |
| Dimethyl distearyl ammonium chloride | — | — | 0.01 |
| Decamethylcyclopentasiloxane | 8.0 | 8.0 | 8.0 |
| Isononyl isonanoate | 5.0 | 5.0 | 5.0 |
| Octyl methoxycinnamate | 5.0 | 5.0 | 5.0 |
| Purified water | Balance | Balance | Balance |
| Evaluation (1) Appearance | Δ | Δ | ○ |
| Evaluation (2) Emulsified particles | X | ○ | ○ |
| Evaluation (3) Skin irritation | ◎ | X | ◎ |
| Evaluation (4) Sticky feeling | ○ | Δ | ○ |

(Production Method)

Glycerin and succinoglycan, which are water phase components, and silica-coated zinc oxide, which is a powder component, were added to purified water and mixed. To this, trimethyl stearyl ammonium chloride or dimethyl distearylammonium chloride that had been separately dispersed in purified water was added, and the ultrasonic wave treatment under heating was carried out. After the powder component was uniformly dispersed, the remaining oil phase component was added and mixed with a mixer until it became uniform, and an oil-in-water emulsion composition was obtained.

As seen from Table 1, in Test Example 1, wherein only powder was blended, the emulsification was significantly poor. In Test Example 2, wherein a small amount of single-chain cationic active agent was added, the emulsification was improved. However, the skin irritation was high, and the sticky feeling tended to be high. In contrast, in Test Example 3, wherein a cationic active agent having two long alkyl chains is added, the emulsification, skin irritation, and sticky feeling were all good.

Subsequently, in order to investigate the preferable blending quantity of powder, the oil-in-water emulsions having the blending compositions listed in Table 2 were produced by the conventional method. The above-described evaluation tests (1) to (4) were performed for each sample.

TABLE 2

|  | Test Example | | | | |
|---|---|---|---|---|---|
|  | 4 | 5 | 6 | 7 | 8 |
| Glycerin | 3.0 | 3.0 | 3.0 | 3.0 | 3.0 |
| Succinoglycan | 0.35 | 0.35 | 0.35 | 0.35 | 0.35 |
| Silica-coated zinc oxide | 0.1 | 1 | 10 | 20 | 30 |
| Dimethyl distearyl ammonium chloride | 0.05 | 0.05 | 0.05 | 0.05 | 0.05 |
| Decamethyl-cyclopentasiloxane | 8.0 | 8.0 | 8.0 | 8.0 | 8.0 |
| Isononyl isonanoate | 5.0 | 5.0 | 5.0 | 5.0 | 5.0 |
| Octyl methoxycinnamate | 5.0 | 5.0 | 5.0 | 5.0 | 5.0 |
| Purified water | Balance | Balance | Balance | Balance | Balance |
| Evaluation (1) Appearance | X | Δ | ○ | ○ | Δ |
| Evaluation (2) Emulsified particles | X | ○ | ○ | ○ | ○ |
| Evaluation (3) Skin irritation | ◎ | ◎ | ◎ | ◎ | ◎ |
| Evaluation (4) Sticky feeling | ○ | ○ | ○ | Δ | X |

(Production Method)

Glycerin and succinoglycan, which are water phase components, and silica-coated zinc oxide, which is a powder component, were added to purified water and mixed. To this, dimethyl distearyl ammonium chloride that had been separately dispersed in purified water was added, and the ultrasonic wave treatment under heating was carried out. After the powder component was uniformly dispersed, the remaining oil phase component was added and mixed with a mixer until it became uniform, and an oil-in-water emulsion composition was obtained.

As seen from Table 2, in Test Examples 5 to 7, the emulsions showed excellent emulsion stability, low sticky feeling, and low skin irritation. On the other hand, in Test Example 4, wherein 0.1 mass % of powder was blended, the emulsion had slightly inferior emulsion stability. In Test Example 8, wherein 30 mass % of powder was blended, the sticky feeling was strong.

Accordingly, in the oil-in-water emulsion of the present invention, it is preferable that the blending quantity of powder is 1 to 20 mass % with respect to the total amount of the emulsion.

Subsequently, in order to investigate the preferable blending quantity of the cationic surfactant having two long-chain alkyl groups, the oil-in-water emulsions having the blending compositions listed in Table 3 were produced by the conventional method. The above-described evaluation tests (1) to (4) were performed for each sample.

TABLE 3

|  | Test Example | | | | |
|---|---|---|---|---|---|
|  | 9 | 10 | 11 | 12 | 13 |
| Glycerin | 3.0 | 3.0 | 3.0 | 3.0 | 3.0 |
| Succinoglycan | 0.35 | 0.35 | 0.35 | 0.35 | 0.35 |
| Silica-coated zinc oxide | 3 | 3 | 3 | 3 | 3 |
| Dimethyl distearyl ammonium chloride | 0.0005 | 0.001 | 0.01 | 0.5 | 1 |
| Decamethyl-cyclopentasiloxane | 8.0 | 8.0 | 8.0 | 8.0 | 8.0 |
| Isononyl isonanoate | 5.0 | 5.0 | 5.0 | 5.0 | 5.0 |
| Octyl methoxycinnamate | 5.0 | 5.0 | 5.0 | 5.0 | 5.0 |
| Purified water | Balance | Balance | Balance | Balance | Balance |
| Evaluation (1) Appearance | X | Δ | ○ | ○ | ○ |
| Evaluation (2) Emulsified particles | X | Δ | ○ | ○ | ○ |
| Evaluation (3) Skin irritation | ◎ | ◎ | ◎ | ○ | Δ |
| Evaluation (4) Sticky feeling | ○ | ○ | ○ | Δ | X |

(Production Method)

Glycerin and succinoglycan, which are water phase components, and silica-coated zinc oxide, which is a powder component, were added to purified water and mixed. To this, dimethyl distearyl ammonium chloride that had been separately dispersed in purified water was added, and the ultrasonic wave treatment under heating was carried out. After the powder component was uniformly dispersed, the remaining oil phase component was added and mixed with a mixer until it became uniform, and an oil-in-water emulsion composition was obtained.

As seen from Table 3, in Test Examples 10 to 12, the emulsions showed excellent emulsion stability, low sticky feeling, and low skin irritation. On the other hand, in Test Example 9, wherein 0.0005 mass % of a cationic surfactant was blended, the emulsion had poor emulsification. Test Example 13, wherein 1 mass % of cationic surfactant was blended, had somewhat high skin irritation, and the sticky feeling was strong.

Accordingly, in the oil-in-water emulsion of the present invention, it is preferable the blending quantity of the cationic surfactant is 0.001 to 0.5 mass % with respect to the total amount of the emulsion.

Subsequently, the oil-in-water emulsions having the blending compositions listed in Table 4 were produced by the conventional method. The above-described evaluation tests (1) to (4) were performed for each sample.

TABLE 4

|  | Test Example | | | |
| --- | --- | --- | --- | --- |
|  | 14 | 15 | 16 | 17 |
| Glycerin | 3.0 | 3.0 | 3.0 | 3.0 |
| Succinoglycan | 0.35 | 0.35 | 0.35 | 0.35 |
| Silica-coated zinc oxide | 3.0 | 3.0 | 3.0 | 3.0 |
| Dimethyl dialkyl (C10) ammonium chloride | 0.05 | — | — | — |
| Dimethyl dialkyl (C12) ammonium chloride | — | 0.05 | — | — |
| Dimethyl dialkyl (C18) ammonium chloride | — | — | 0.05 | — |
| Dimethyl dialkyl (C22) ammonium chloride | — | — | — | 0.05 |
| Decamethylcyclopentasiloxane | 8.0 | 8.0 | 8.0 | 8.0 |
| Isononyl isonanoate | 5.0 | 5.0 | 5.0 | 5.0 |
| Octyl methoxycinnamate | 5.0 | 5.0 | 5.0 | 5.0 |
| Purified water | Balance | Balance | Balance | Balance |
| Evaluation (1) Appearance | X | ○ | ○ | ○ |
| Evaluation (2) Emulsified particles | X | ○ | ○ | ○ |
| Evaluation (3) Skin irritation | Δ | ◎ | ◎ | ◎ |
| Evaluation (4) Sticky feeling | ○ | ○ | ○ | Δ |

(Production Method)

Glycerin and succinoglycan, which are water phase components, and silica-coated zinc oxide, which is a powder component, were added to purified water and mixed. To this, dimethyl distearyl ammonium chloride that had been separately dispersed in purified water was added, and the ultrasonic wave treatment under heating was carried out. After the powder component was uniformly dispersed, the remaining oil phase component was added and mixed with a mixer until it became uniform, and an oil-in-water emulsion composition was obtained.

As seen from Table 4, in Test Examples 15 to 17, the emulsions showed excellent emulsion stability, low sticky feeling, and low skin irritation. On the other hand, in Test Example 14, wherein the chain length was 10, the emulsion had poor emulsification. With an increase in the chain length to 18-22 (Test Examples 16 to 17), the sticky feeling became higher.

Accordingly, in the oil-in-water emulsion of the present invention, it is preferable that the length of two alkyl chains of the cationic active agent is 12 to 22.

Then, the time-dependent change of emulsion stability of the oil-in-water emulsion composition was evaluated by blending succinoglycan, xanthan gum, or acrylamide. The evaluation method was as follows.

Evaluation (5): Stability Over Time

The oil-in-water emulsion compositions having the blending compositions listed in Table 5 were produced. One month after the production, the emulsion appearance, of the composition of each test example, was observed by the naked eye.

◎: The composition maintained the emulsion appearance of the production time.

O: Some settlement of the emulsion was observed; however, the composition nearly maintained the emulsion appearance.

Δ: Emulsified particles settled, and the coalescence of particles was also observed.

X: Emulsified particles in the composition settled and coalescenced, and the oil phase separated completely.

TABLE 5

|  | Test Example | | | | |
| --- | --- | --- | --- | --- | --- |
|  | 18 | 19 | 20 | 21 | 22 |
| Glycerin | 3.0 | 3.0 | 3.0 | 3.0 | 3.0 |
| Succinoglycan | 0.35 | — | — | — | — |
| Xanthan gum | — | 0.35 | — | — | — |
| Acrylamido | — | — | 0.35 | — | — |
| Polyacrylate | — | — | — | 0.35 | — |
| Silica-coated zinc oxide (30 nm) | 3.0 | 3.0 | 3.0 | 3.0 | 3.0 |
| Dimethyl distearyl ammonium chloride | 0.05 | 0.05 | 0.05 | 0.05 | 0.05 |
| Decamethyl-cyclopentasiloxane | 8.0 | 8.0 | 8.0 | 8.0 | 8.0 |
| Isononyl isonanoate | 5.0 | 5.0 | 5.0 | 5.0 | 5.0 |
| Octyl methoxycinnamate | 5.0 | 5.0 | 5.0 | 5.0 | 5.0 |
| Purified water | Balance | Balance | Balance | Balance | Balance |
| Evaluation (5) Stability over time | ○ | ○ | ○ | Δ | Δ |

(Production Method)

Glycerin and succinoglycan, xanthan gum, acrylamide, or a polyacrylic acid salt, which are water phase components, and silica-coated zinc oxide, which is a powder component, were added to purified water and mixed. To this, dimethyl distearyl ammonium chloride that had been separately dispersed in purified water was added, and the ultrasonic wave treatment under heating was carried out. After the powder component was uniformly dispersed, the remaining oil phase component was added and mixed with a mixer until it became uniform, and an oil-in-water emulsion composition was obtained.

As shown in Table 5, in Test Examples 18 to 20, wherein succinoglycan, xanthan gum, or acrylamide was blended, a stable emulsion appearance was maintained over a long period. In contrast, Test Example 21, wherein some other thickener was blended, and Test Example 22, wherein no thickener is blended, became slightly less stable over time.

Accordingly, in the oil-in-water emulsion composition of the present invention, it is preferable to blend one or more selected from the group consisting of succinoglycan, xanthan gum, and acrylamide.

The production method of the oil-in-water emulsion composition of the present invention was investigated. According to the below-described respective production methods, the emulsion compositions having formulations shown in Table 6 were produced, and the emulsion state was evaluated. The results are shown in Table 7.

Production Method (Test Example 23)

A water phase component, a powder component that was uniformly dispersed in a portion of purified water, and a surfactant component that was uniformly dispersed in the remaining purified water were mixed, and the ultrasonic wave treatment was carried out under heating at 70° C. Into this, an oil phase component that was heated to 70° C. was added, and the composition was obtained by the emulsification with an emulsifying machine.

(Test Example 24)

A water phase component and a powder component were mixed, and the ultrasonic wave treatment was carried out under heating at 70° C. Into this, an oil phase component that was heated to 70° C. and a surfactant component were added, and the composition was obtained by the emulsification with an emulsifying machine.
(Test Example 25)

A powder and a surfactant component were stirred in a suitable amount of ethanol; then the surfactant treated powder was obtained by evaporating ethanol. The surfactant-treated powder and a water phase component were mixed, and the ultrasonic wave treatment was carried out under heating at 70° C. Into this, an oil phase component that was heated to 70° C. was added, and the composition was obtained by the emulsification with an emulsifying machine.

Evaluation Methods
Evaluation (1): Emulsion Stability (Appearance)
The appearance of the emulsion was observed by the naked eye within 1 day of the preparation of the emulsion.
- O: The sample was uniform, and the oil floatation or powder aggregation was not observed.
- Δ: The sample was nearly uniform; however, some oil floatation was observed.
- X: The sample was not uniform, or a significant separation of the oil phase or the powder aggregation was observed.

Evaluation (2): Emulsion Stability (Emulsified Particles)
When the sample was observed with an optical microscope,
- O: Emulsified particles were uniform, and the coalescence or aggregation was not observed.
- Δ: Emulsified particles were nearly uniform; however, slight coalescence or aggregation was observed.
- X: Emulsified particles were not uniform, and significant coalescence or aggregation was observed.

TABLE 6

| (Water components) | |
|---|---|
| Glycerin | 3.0 |
| Succinoglycan | 0.35 |
| Purified water | Balance |
| (Powder component) | |
| Silica-coated zinc oxide (30 nm) | 3.0 |
| (Surfactant component) | |
| Dimethyl distearyl ammonium chloride | 0.05 |
| (Oil components) | |
| Decamethylcyclopentasiloxane | 8.0 |
| Isononyl isonanoate | 5.0 |
| Octyl methoxycinnamate | 5.0 |

TABLE 7

| | Test Example | | |
|---|---|---|---|
| | 23 | 24 | 25 |
| Evaluation (1) Appearance | O | Δ | Δ |
| Evaluation (2) Emulsified particles | O | Δ | Δ |

As shown in Table 7, Test Example 23, wherein a specific cationic surfactant dispersed in water was mixed with a powder component and the emulsification with an oil phase component was subsequently carried out, showed excellent emulsion stability.

On the other hand, in Test Example 24, wherein a cationic surfactant was added, without going through the above process, at the time of emulsification of a water phase and an oil phase, a stable emulsion could not be obtained, and the coalescence or aggregation of oil droplets or powder was observed. In addition, in Test Example 25, wherein a separate treatment was carried out in ethanol instead of the treatment of powder and a cationic surfactant in water, the emulsion stability was poor.

From the comparison of Test Examples 23 and 24, it is clear that a stable emulsion can be obtained by forming lamellar liquid crystals through the dispersion of a specific cationic surfactant in water, adsorbing them on powder particles, and subsequently carrying out emulsification. In addition, from the comparison of Test Examples 23 and 25, it was found that a composition with high emulsion stability could be easily produced by treating the powder with a specific cationic surfactant that formed lamellar liquid crystals in water.

The emulsion stability was evaluated for the composition obtained by mixing 50 parts by weight of the surface-treated-powder dispersion liquid, which was obtained by each method described below, and 50 parts by weight of the oil phase component (liquid paraffin) under heating at 70° C.
(Test Example 26)

Into 100 parts by weight of water, 0.1 parts by weight of dimethyl distearyl ammonium chloride and 6 parts by weight of silica-coated zinc oxide were dispersed, and ultrasonic wave treatment was carried out under heating.
(Test Example 27)

Into 100 parts by weight of ethanol, 0.1 parts by weight of stearic acid was dissolved. To the obtained solution, 6 parts by weight of silica-coated zinc oxide was added, and the mixing with stirring was carried out under heating.
(Test Example 28)

Into 100 parts by weight of water, 0.1 parts by weight of glyceryl monostearate was uniformly dispersed, 6 parts by weight of silica-coated zinc oxide was added and dispersed, and ultrasonic wave treatment was carried out under heating.

TABLE 8

| | Test Example | | |
|---|---|---|---|
| | 26 | 27 | 28 |
| Evaluation(1) Appearance | O | Δ | Δ |
| Evaluation(2) Emulsified particles | O | X | X |

As shown in Test Example 26, an O/P/W emulsion composition excellent in stability could be obtained by treating the powder with dimethyl distearyl ammonium chloride in water and carrying out the powder emulsification of the oil phase component with the use of the obtained dispersion liquid of the treated powder.

On the other hand, the powder treatment with stearic acid, which is a common hydrophobizing agent of powder, was carried out in ethanol because the treatment in water is difficult because of its properties (Test Example 27). Therefore, the emulsification could not be carried out for the dispersion of the treated powder, as it is, and the oil phase component. The treated powder was redispersed in water and the emulsification was tried. As a result, it was found that the powder emulsification was possible; however, the emulsion stability of the obtained composition was inferior to that of Test Example 26.

In Test Example 28, it was possible to form treated powder in water with the use of glyceryl monostearate and to carry out the powder emulsification with the use of the dispersion liquid. However, the emulsion stability of the obtained composition was inferior to that of Test Example 26.

Based on the above results, it is possible to obtain the oil-in-water emulsion composition of the present invention by using a cationic surfactant having two long-chain alkyl groups as the treatment agent of the powder, which is involved in emulsification, treating the powder in water, and mixing the dispersion liquid of the obtained treated powder, as it is, and the oil phase component. That is, in the production of the oil-in-water emulsion composition of the present invention, it is possible to carry out, easily and continuously, the operations starting from the surface treatment of the powder to the emulsification with the powder by using a cationic surfactant having a specific structure as the powder treatment agent, and the emulsion stability is high.

Additionally, in the formulations in Table 6, the compositions which had been prepared by adding the following blending quantities of hydrophilic surfactant (PEG-60 hydrogenated castor oil) in the following methods were evaluated. The results are shown in Table 9.

Production Process of Compositions
(A) A water phase component, a powder component that was uniformly dispersed in a portion of purified water, and a surfactant component (dimethyl distearyl ammonium chloride) that was uniformly dispersed in the remaining purified water were mixed, and the ultrasonic wave treatment was carried out under heating at 70° C.
(B) Into the aforementioned dispersion, an oil phase component that was heated to 70° C. was added, and emulsified with an emulsifying machine.

Method of Adding Hydrophilic Surfactant
(Test Example 29)
In the aforementioned process (B), 0.01 mass % of hydrophilic surfactant (PEG-60 hydrogenated castor oil) with respect to the total components was added and mixed after the emulsification.
(Test Example 30)
In the aforementioned process (B), 1 mass % of hydrophilic surfactant (PEG-60 hydrogenated castor oil) with respect to the total components was added and mixed after the emulsification.
(Test Example 31)
In the aforementioned process (A), 0.01 mass % of hydrophilic surfactant (PEG-60 hydrogenated castor oil) with respect to the total components was added as a water phase component.
(Test Example 32)
In the aforementioned process (A), 1 mass % of hydrophilic surfactant (PEG-60 hydrogenated castor oil) with respect to the total components was added as a water phase component.

Evaluation Methods
Evaluation (1): Emulsion Stability (Appearance)
The appearance of the emulsion was observed by the naked eye within 1 day of the preparation of the emulsion.
O: The sample was uniform, and the oil floatation or powder aggregation was not observed.
Δ: The sample was nearly uniform; however, some oil floatation was observed.
X: The sample was not uniform, or a significant separation of the oil phase or the powder aggregation was observed.
Evaluation (2): Emulsion Stability (Emulsified Particles)
When the sample was observed with an optical microscope,
O: Emulsified particles were uniform, and the coalescence or aggregation was not observed.
Δ: Emulsified particles were nearly uniform; however, slight coalescence or aggregation was observed.
X: Emulsified particles were not uniform, and significant coalescence or aggregation was observed.

Evaluation (3): Skin Irritation Test
A 24-hour occlusive patch test was performed on the medial side of the upper arm of 10 panelists, and the average value was calculated based on the following criteria.
0 . . . No abnormality was observed.
1 . . . . Slight redness was observed.
2 . . . . Redness was observed.
3 . . . . Redness and papules were observed.
The evaluation criteria for the "skin irritation test" were as follows.
⊚: The average value of 10 panelists was 0 or higher and less than 0.15.
O: The average value of 10 panelists was 0.15 or higher and less than 0.2.
Δ: The average value of 10 panelists was 0.2 or higher and less than 0.3.
X: The average value of 10 panelists was 0.3 or higher.
Evaluation (4): Affinity of Skin after Application
Each sample was evaluated with an actual use test by 10 professional panelists. The evaluation criteria are as follows.
⊚: 8 or more panelists acknowledged that affinity of skin after application is good.
O: 6 or more and less than 8 panelists acknowledged that affinity of skin after application is good.
Δ: 3 or more and less than 6 panelists acknowledged that affinity of skin after application is good.
X: Less than 3 panelists acknowledged that affinity of skin after application is good.

TABLE 9

|  | Test Example | | | | |
| --- | --- | --- | --- | --- | --- |
|  | 23 | 29 | 30 | 31 | 32 |
| Evaluation (1) Appearance | O | O | O | O | O |
| Evaluation (2) Emulsified particles | O | O | O | O | O |
| Evaluation (3) Skin irritation | ⊚ | ⊚ | Δ | ⊚ | Δ |
| Evaluation (6) Affinity of skin | Δ | ⊚ | ⊚ | Δ | Δ |

According to Table 9, Test Example 29, wherein 0.01 mass % of hydrophilic surfactant was added after the emulsification process, retained the equivalent level of low skin irritation to Test Example 23, wherein no hydrophilic surfactant was added, and showed a highly-improved affinity of skin. However, the skin irritation in Test Example 30, wherein 1 mass % of hydrophilic surfactant was added in the same addition method, was inferior to that of Test Example 25.

On the other hand, the compositions in Test Examples 31 and 32, wherein hydrophilic surfactant was respectively added during treating powder, did not show improved affinity of skin. However, they showed deteriorations of the skin irritation owing to the increased additive amount which is to those in Test Examples 29 and 30.

When a hydrophilic surfactant was added after carrying out sufficient powder emulsification, it was impossible for the hydrophilic surfactant to act on the interface because the powders had already absorbed on the surface of emulsified oil droplets. Thus, it can be understood that the hydrophilic surfactant was dissolved and dispersed into the external water phase and contributed to the improved affinity of skin. On the other hand, when a hydrophilic surfactant was added during the surface treatment of the powder, it can be understood that the effect of affinity of skin was not achieved in the water phase because the surfactant acted on the interface during the successive emulsification process.

From the above-mentioned results, it was found that, in the oil-in-water emulsion composition according to the present invention, affinity of skin after application is improved by blending the hydrophilic surfactant to the extent that it does not affect on the emulsification process or skin irritation: As the result of further investigation, the range of blending quantity of hydrophilic surfactant, which can achieve the aforementioned effects, is 0.001 to 0.5 mass % with respect to the composition, preferably 0.01 to 0.5 mass %.

In the following, formulation examples of the oil-in-water emulsion composition of the present invention are listed. However, the present invention is not limited to these examples. All the oil-in-water emulsion compositions obtained in the below-described formulation examples had high emulsion stability, a low sticky feeling, and low skin irritation.

Formulation example 1: Milky lotion

| | (mass %) |
|---|---|
| Phase A | |
| Squalane | 4.0 |
| Oleyl oleate | 2.5 |
| Sorbitan sesquioleate | 0.8 |
| Evening primrose oil | 0.2 |
| Perfume | 0.1 |
| Phase B | |
| 1,3-butylene glycol | 1.5 |
| Ethanol | 2.0 |
| Silica (10 nm) | 5.0 |
| Dimethyl distearyl ammonium chloride | 0.05 |
| Purified water | Q.S. |
| Phase C | |
| Xanthan gum | 0.1 |
| Purified water | Q.S. |
| Phase D | |
| Carboxyvinyl polymer | 0.2 |
| Potassium hydroxide | 0.1 |
| L-Arginine L-aspartate | 0.01 |
| PEG-100 hydrogenated castor oil | 0.05 |
| Edetate | 0.05 |
| Antiseptic | Q.S. |
| Purified water | Balance |

(Production Method)

A milky lotion was obtained by heating Phase B to 70° C., dispersing sufficiently with a mixer or by ultrasonic wave, adding phase C, adding phase A and emulsifying with an emulsifying machine, and lastly adding phase D.

Formulation example 2: UV-protecting milky lotion

| | (mass %) |
|---|---|
| Phase A | |
| Squalane | 4.0 |
| Octyl methoxycinnamate | 8.0 |
| Cyclopentadimethylsiloxane | 5.0 |
| Perfume | 0.1 |
| Phase B | |
| 1,3-butylene glycol | 1.5 |
| Ethanol | 2.0 |
| Silica-coated zinc oxide (30 nm) | 3.0 |
| Dimethyl distearyl ammonium chloride | 0.015 |
| Purified water | Q.S. |
| Phase C | |
| Succinoglycan | 0.2 |
| Glycerin | 3.0 |
| PEG-60 hydrogenated castor oil | 0.01 |
| L-Arginine L-aspartate | 0.01 |
| Edetate | 0.05 |
| Antiseptic | Q.S. |
| Purified water | Balance |

(Production Method)

Phase B was heated to 70° C. and dispersed with a mixer or by ultrasonic wave. Subsequently, uniformly dissolved phase C was added to this. Phase A heated to 70° C. was added to phase B heated to 70° C., and the emulsification was carried out with an emulsifying machine. This was cooled and a milky lotion was obtained.

Formulation example 3: foundation

| | (mass %) |
|---|---|
| Phase A | |
| Cetanol | 3.5 |
| Deodorized lanolin | 4.0 |
| Jojoba oil | 5.0 |
| Petrolatum | 2.0 |
| Squalane | 6.0 |
| Pyridoxine tripalmitate | 0.1 |
| Antiseptic | Q.S. |
| Perfume | 0.3 |
| Phase B | |
| Mica | 5.0 |
| Dimethyl distearyl ammonium chloride | 0.015 |
| Purified water | Q.S. |
| Phase C | |
| Propylene glycol | 10.0 |
| POE(30)behenyl ether | 0.02 |
| Prepared powder | 12.0 |
| Trisodium edetate | 0.5 |
| Purified water | Balance |

(Production Method)

Phase B was heated to 70° C. and sufficiently dispersed with an emulsifying machine, subsequently heated phase A was added, and the emulsification was carried out with an emulsifying machine. Lastly Phase C was added, and a foundation was obtained by cooling the emulsion with a heat exchanger.

All the oil-in-water emulsion compositions of Formulation Examples 1 to 3 were excellent in emulsion stability, and the skin irritation and stickiness were absent.

EXAMPLE 2

In the following, the external skin preparation for sunscreen of the present invention was discussed. In the examples, "mass %" or "%", which represents the blending quantity, indicates mass % with respect to the total amount of the composition unless otherwise noted.

Initially, the evaluation methods used in the present examples will be explained.

Evaluation (1): Emulsion Stability (Emulsified Particles)

When the sample appearance was observed with an optical microscope within 1 day after emulsion preparation, O: Emulsified particles were uniform, and the coalescence or aggregation was not observed.

Δ: Emulsified particles were nearly uniform; however, slight coalescence or aggregation was observed.

X: Emulsified particles were not uniform, and significant coalescence or aggregation was observed.

Evaluation (2): Rotation Test

A sample was placed in 50 mL sample tube (diameter: 3 cm), the tube was rotated at 45 rpm for 4 hours at room temperature, and the emulsion stability was evaluated under a microscope. The evaluation criteria were as follows.

O: Emulsified particles were uniform and coalescence was not observed.

Δ: Emulsified particles were nearly uniform; however, slight coalescence was observed.

X: Emulsified particles were not uniform and significant coalescence was observed.

Evaluation (3): Frictional Feeling after Use

The actual usage test by 10 professional panelists was performed for the presence or absence of frictional feeling after the use of each sample. The evaluation criteria were as follows.

⊚: 8 or more panelists acknowledged that there was no frictional feeling after use.

O: 6 or more and less than 8 panelists acknowledged that there was no frictional feeling after use.

Δ: 3 or more and less than 6 panelists acknowledged that there was no frictional feeling after use.

X: less than 3 panelists acknowledged that there was no frictional feeling after use.

Evaluation (4): Evaluation of Sticky Feeling Upon Application

The actual usage test of each sample was performed by 10 professional panelists. The evaluation criteria were as follows.

⊚: 8 or more panelists acknowledged that there was no sticky feeling upon application.

O: 6 or more and less than 8 panelists acknowledged that there was no sticky feeling upon application.

Δ: 3 or more and less than 6 panelists acknowledged that there was no sticky feeling upon application.

X: less than 3 panelists acknowledged that there was no sticky feeling upon application.

External skin preparations for sunscreen having the blending compositions listed in Table 10 were produced, and the above-described evaluation tests (1) to (4) were performed for each sample.

TABLE 10

|  | Test Example | | | | | |
|---|---|---|---|---|---|---|
|  | 33 | 34 | 35 | 36 | 37 | 38 |
| (Phase A) | | | | | | |
| Ion-exchanged water | Balance | Balance | Balance | Balance | Balance | Balance |
| Stearyl trimethyl ammonium chloride | — | 0.05 | — | — | — | — |
| Dimethyl distearyl ammonium chloride | — | — | 0.05 | 0.05 | 0.05 | 0.05 |
| Silica-coated zinc oxide (30 nm) | 3.0 | 3.0 | 3.0 | — | 3.0 | 3.0 |
| Hydrophilic titanium dioxide | — | — | — | — | — | 5.0 |
| (Phase B) | | | | | | |
| Ion-exchanged water | Portion | Portion | Portion | Portion | Portion | Portion |
| Glycerin | 3.0 | 3.0 | 3.0 | 3.0 | 3.0 | 3.0 |
| Succinoglycan | 0.35 | 0.35 | 0.35 | 0.35 | 0.35 | 0.35 |
| Antiseptic | Q.S. | Q.S. | Q.S. | Q.S. | Q.S. | Q.S. |
| (Phase C) | | | | | | |
| Decamethylcyclopentasiloxane | 8.0 | 8.0 | 8.0 | 8.0 | 8.0 | 8.0 |
| Isononyl isonanoate | 5.0 | 5.0 | 5.0 | 5.0 | 5.0 | 5.0 |
| Octyl methoxycinnamate | 5.0 | 5.0 | 5.0 | 5.0 | 5.0 | 5.0 |
| Hydrophobized titanium dioxide | 5.0 | 5.0 | 5.0 | 5.0 | — | — |
| Evaluation (1) Emulsion stability | X | O | O | X | O | O |
| Evaluation (2) Rotation test | X | Δ | O | X | O | O |
| Evaluation (3) Frictional feeling after use | — | O | ⊚ | — | Δ | X |
| Evaluation (4) Sticky feeling upon application | — | O | ⊚ | — | Δ | X |

(Production Method)

Phase A was heated to 70° C. and was dispersed by ultrasonic wave, and uniformly dissolved phase B was added. Phase C heated to 70° C. was added to phase B heated to 70° C., the emulsification was carried out with an emulsifying machine, and then emulsion was cooled to room temperature.

As shown in Table 10, in Test Example 33, wherein the powder was used without blending a cationic surfactant, the emulsification was significantly poor. In Test Example 34, wherein only a single-chain cationic surfactant was added, a decrease in the rotation emulsion stability was observed. In contrast, in Test Example 35, wherein a cationic surfactant having two long alkyl chains was added, excellent results in all items were shown.

In Test Example 36, wherein a powder component (silica-coated zinc oxide) was not blended, the emulsion stability was significantly poorer compared with that of Test Example 35. In Test Example 37, wherein a hydrophobized powder is not contained in the oil phase, a frictional feeling was present after use, and the stickiness tends to be present upon application. In Test Example 38, wherein hydrophilic titanium dioxide instead of the hydrophobized powder was blended, a significant frictional feeling and sticky feeling were present.

From the above results, it was found that the excellent emulsion stability could be provided to the oil-in-water external skin preparation for sunscreen of the present invention by including an oil-in-water emulsion composition containing (a) a powder component, (b) a cationic surfactant having two alkyl chains with 12 or more and 22 or less carbon atoms, (c) an oil phase component, and (d) a water phase component. In addition, the frictional feeling after use and the sticky feeling during application can be improved by blending a hydrophobized powder in the oil phase component.

Subsequently, in order to investigate the preferable blending quantity of the powder used for emulsification, external skin preparations for sunscreen having the blending compositions listed in Table 11 were produced, and the above-described evaluation tests (1) to (4) were performed for each sample.

As seen from Table 11, the compositions of Test Examples 40 to 42 had excellent emulsion stability, and a frictional feeling and sticky feeling were nearly absent. On the other hand, Test Example 39, wherein 0.5 mass % of powder was blended, had poor emulsion stability. In Example 43, wherein 30 mass % of powder was blended, a strong frictional feeling and sticky feeling were present.

Accordingly, in the external skin preparation for sunscreen of the present invention, it is preferable that the blending quantity of powder is 1 to 20 mass % with respect to the total amount of an external preparation.

TABLE 11

|  | Test Example ||||| 
| --- | --- | --- | --- | --- | --- |
|  | 39 | 40 | 41 | 42 | 43 |
| (Phase A) | | | | | |
| Ion-exchanged water | Balance | Balance | Balance | Balance | Balance |
| Dimethyl distearyl ammonium chloride | 0.05 | 0.05 | 0.05 | 0.05 | 0.05 |
| Silica-coated zinc oxide (30 nm) | 0.5 | 1.0 | 5.0 | 20.0 | 30.0 |
| (Phase B) | | | | | |
| Ion-exchanged water | Portion | Portion | Portion | Portion | Portion |
| Glycerin | 3.0 | 3.0 | 3.0 | 3.0 | 3.0 |
| Succinoglycan | 0.35 | 0.35 | 0.35 | 0.35 | 0.35 |
| Antiseptic | Q.S. | Q.S. | Q.S. | Q.S. | Q.S. |
| (Phase C) | | | | | |
| Decamethylcyclopentasiloxane | 8.0 | 8.0 | 8.0 | 8.0 | 8.0 |
| Isononyl isononanoate | 5.0 | 5.0 | 5.0 | 5.0 | 5.0 |
| Octyl methoxycinnamate | 5.0 | 5.0 | 5.0 | 5.0 | 5.0 |
| Hydrophobized titanium dioxide | 5.0 | 5.0 | 5.0 | 5.0 | 5.0 |
| Evaluation (1) Emulsion stability | X | ○ | ○ | ○ | ○ |
| Evaluation (2) Rotation test | X | ○ | ○ | ○ | ○ |
| Evaluation (3) Frictional feeling after use | — | ◎ | ◎ | ○ | X |
| Evaluation (4) Sticky feeling upon application | — | ◎ | ◎ | ○ | X |

(Production Method)

Phase A was heated to 70° C. and was dispersed by ultrasonic wave, and uniformly dissolved phase B was added. Phase C heated to 70° C. was added to phase B heated to 70° C., the emulsification was carried out with an emulsifying machine, and then emulsion was cooled to room temperature.

Subsequently, in order to investigate the preferable blending quantity of the cationic surfactant having two long-chain alkyl groups, oil-in-water external skin preparations for sunscreen having the blending compositions listed in Table 12 were produced, and the above-described evaluation tests (1) to (4) were performed for each sample.

TABLE 12

|  | Test Example ||||| 
| --- | --- | --- | --- | --- | --- |
|  | 44 | 45 | 46 | 47 | 48 |
| (Phase A) | | | | | |
| Ion-exchanged water | Balance | Balance | Balance | Balance | Balance |
| Dimethyl distearyl ammonium chloride | 0.0005 | 0.001 | 0.05 | 0.5 | 0.1 |
| Silica-coated zinc oxide (30 nm) | 3.0 | 3.0 | 3.0 | 3.0 | 3.0 |
| (Phase B) | | | | | |
| Ion-exchanged water | Portion | Portion | Portion | Portion | Portion |
| Glycerin | 3.0 | 3.0 | 3.0 | 3.0 | 3.0 |
| Succinoglycan | 0.35 | 0.35 | 0.35 | 0.35 | 0.35 |
| Antiseptic | Q.S. | Q.S. | Q.S. | Q.S. | Q.S. |
| (Phase C) | | | | | |
| Decamethylcyclopentasiloxane | 8.0 | 8.0 | 8.0 | 8.0 | 8.0 |
| Isononyl isononanoate | 5.0 | 5.0 | 5.0 | 5.0 | 5.0 |
| Octyl methoxycinnamate | 5.0 | 5.0 | 5.0 | 5.0 | 5.0 |
| Hydrophobized titanium dioxide | 5.0 | 5.0 | 5.0 | 5.0 | 5.0 |

TABLE 12-continued

| | Test Example | | | | |
|---|---|---|---|---|---|
| | 44 | 45 | 46 | 47 | 48 |
| Evaluation (1) Emulsion stability | X | ○ | ○ | ○ | X |
| Evaluation (2) Rotation test | — | ○ | ○ | ○ | — |
| Evaluation (3) Frictional feeling after use | — | ◎ | ◎ | ◎ | — |
| Evaluation (4) Sticky feeling upon application | — | ◎ | ◎ | ◎ | — |

(Production Method)

Phase A was heated to 70° C. and was dispersed by ultrasonic wave, and uniformly dissolved phase B was added. Phase C heated to 70° C. was added to phase B heated to 70° C., the emulsification was carried out with an emulsifying machine, and then emulsion was cooled to room temperature.

As shown in Table 12, the compositions of Test Examples 45 to 47 had excellent emulsion stability, and no frictional feeling and no sticky feeling were present. On the other hand, in Example 44, wherein 0.0005 mass % of a cationic surfactant was blended, and in Test Example 48, wherein 1 mass % of a cationic surfactant was blended, the emulsion stability was significantly poor.

Accordingly, in the external skin preparation for sunscreen of the present invention, it is preferable that the blending quantity of a cationic surfactant having two alkyl chains with 12 or more and 22 or less carbon atoms is 0.001 to 0.5 mass % with respect to the amount of total components.

In addition, external skin preparations for sunscreen having the blending compositions listed in Table 13 were produced, and the above-described evaluation tests (1) to (4) were performed for each sample.

TABLE 13

| | Test Example | | | |
|---|---|---|---|---|
| | 49 | 50 | 51 | 52 |
| (Phase A) | | | | |
| Ion-exchanged water | Balance | Balance | Balance | Balance |
| Dimethyl dialkyl (C10) ammonium chloride | 0.05 | — | — | — |
| Dimethyl dialkyl (C12) ammonium chloride | — | 0.05 | — | — |
| Dimethyl dialkyl (C18) ammonium chloride | — | — | 0.05 | — |
| Dimethyl dialkyl (C22) ammonium chloride | — | — | — | 0.05 |
| Silica-coated zinc oxide (30 nm) | 3.0 | 3.0 | 3.0 | 3.0 |
| (Phase B) | | | | |
| Ion-exchanged water | Portion | Portion | Portion | Portion |
| Glycerin | 3.0 | 3.0 | 3.0 | 3.0 |
| Succinoglycan | 0.35 | 0.35 | 0.35 | 0.35 |
| Antiseptic | Q.S. | Q.S. | Q.S. | Q.S. |
| (Phase C) | | | | |
| Decamethylcyclopentasiloxane | 8.0 | 8.0 | 8.0 | 8.0 |
| Isononyl isononanoate | 5.0 | 5.0 | 5.0 | 5.0 |
| Octyl methoxycinnamate | 5.0 | 5.0 | 5.0 | 5.0 |
| Hydrophobized titanium dioxide | 5.0 | 5.0 | 5.0 | 5.0 |
| Evaluation(1) Emulsion stability | X | ○ | ○ | ○ |
| Evaluation(2) Rotation test | X | ○ | ○ | Δ |
| Evaluation(3) Frictional feeling after use | — | ◎ | ◎ | ○ |
| Evaluation(4) Sticky feeling upon application | — | ◎ | ◎ | Δ |

(Production Method)

Phase A was heated to 70° C. and was dispersed by ultrasonic wave, and uniformly dissolved phase B was added. Phase C heated to 70° C. was added to phase B heated to 70° C., the emulsification was carried out with an emulsifying machine, and then emulsion was cooled to room temperature.

As shown in Table 13, Test Examples 50 and 51 showed good results in all evaluation items. On the other hand, Example 49, wherein a cationic surfactant with a chain length of 10 was blended, was poor in emulsion stability. When a cationic surfactant with a chain length of 22 or higher was blended, as in Test Example 52, the emulsion stability during rotation decreased, and the frictional feeling and sticky feeling increased.

Accordingly, in the external skin preparation for sunscreen of the present invention, the length of two alkyl chains of the cationic surfactant is preferably 12 to 22.

In the following, formulation examples of the external skin preparation for sunscreen of the present invention are listed. However, the present invention is not limited to these examples. All the oil-in-water external skin preparations for sunscreen obtained in the below-described formulation examples had high emulsion stability and water resistance, a low frictional feeling and sticky feeling, and low skin irritation.

Formulation example 1: sunscreen milky lotion

| | (mass %) |
|---|---|
| Phase A | |
| Squalane | 4.0 |
| Oleyl oleate | 2.5 |
| Sorbitan sesquioleate | 0.8 |
| Evening primrose oil | 0.2 |
| Hydrophobized titanium dioxide | 3.0 |
| Perfume | 0.1 |
| Phase B | |
| 1,3-butylene glycol | 1.5 |
| Ethanol | 2.0 |
| Silica (10 nm) | 5.0 |
| Dimethyl distearyl ammonium chloride | 0.05 |
| Purified water | Q.S. |
| Phase C | |
| Xanthan gum | 0.1 |
| Purified water | Q.S. |
| Phase D | |
| Carboxyvinyl polymer | 0.2 |
| Potassium hydroxide | 0.1 |
| PEG-100 hydrogenated castor oil | 0.01 |
| L-Arginine L-aspartate | 0.01 |
| Edetate | 0.05 |
| Antiseptic | Q.S. |
| Purified water | Balance |

(Production Method)

A milky lotion was obtained by heating Phase B to 70° C., dispersing sufficiently with a mixer or by ultrasonic wave, adding phase C, adding phase A and emulsifying with an emulsifying machine, and lastly adding phase D.

| Formulation example 2: UV-protecting milky lotion | |
| --- | --- |
| | (mass %) |
| Phase A | |
| Squalane | 4.0 |
| Octyl methoxycinnamate | 8.0 |
| Cyclopentadimethylsiloxane | 5.0 |
| Hydrophobized zinc oxide | 5.0 |
| Perfume | 0.1 |
| Phase B | |
| 1,3-butylene glycol | 1.5 |
| Ethanol | 2.0 |
| Silica-coated zinc oxide (30 nm) | 3.0 |
| Distearoylethyl dimonium chloride | 0.015 |
| Purified water | Q.S. |
| Phase C | |
| Succinoglycan | 0.2 |
| Glycerin | 3.0 |
| POE(20)behenyl alcohol | 0.02 |
| L-Arginine L-aspartate | 0.01 |
| Edetate | 0.05 |
| Antiseptic | Q.S. |
| Purified water | Balance |

(Production Method)

Phase B was heated to 70° C. and dispersed with a mixer or by ultrasonic wave. Subsequently, uniformly dissolved phase C was added to this. Phase A heated to 70° C. was added to phase B heated to 70° C., and the emulsification was carried out with an emulsifying machine. This was cooled and a milky lotion was obtained.

| Formulation example 3: sunscreen foundation | |
| --- | --- |
| | (mass %) |
| Phase A | |
| Cetanol | 3.5 |
| Deodorized lanolin | 4.0 |
| Jojoba oil | 5.0 |
| Petrolatum | 2.0 |
| Squalane | 6.0 |
| Pyridoxine tripalmitate | 0.1 |
| Hydrophobized titanium dioxide | 3.0 |
| Antiseptic | Q.S. |
| Perfume | 0.3 |
| Phase B | |
| Mica | 5.0 |
| Dimethyl distearyl ammonium chloride | 0.015 |
| Purified water | Q.S. |
| Phase C | |
| Propylene glycol | 10.0 |
| PEG-100 hydrogenated castor oil | 0.05 |
| Prepared powder | 12.0 |
| Trisodium edetate | 0.5 |
| Purified water | Balance |

(Production Method)

Phase B was heated to 70° C. and sufficiently dispersed with an emulsifying machine, subsequently heated phase A was added, and the emulsification was carried out with an emulsifying machine. Lastly Phase C was added, and a foundation was obtained by cooling the emulsion with a heat exchanger.

EXAMPLE 3

The makeup composition of the present invention is discussed. In the examples, "mass %" or "%", which represents the blending quantity, indicates mass % with respect to the total amount of the composition unless otherwise noted.

Initially, the evaluation methods used in the present examples will be explained.

Evaluation (1): Formulation Stability

Prepared emulsions were stored for 1 month at 50° C., and their appearance was observed by the naked eye. In addition, the state of the emulsion was observed with an optical microscope. The evaluation criteria were as follows.

O: No change was observed on appearance, emulsified particles were uniform, and no coalescence or aggregation was observed.

Δ: No change was observed on appearance; however, the coalescence or aggregation of emulsified particles was observed.

X: The separation of the oil phase was observed on appearance.

Evaluation (2): Sticky Feeling after Use

The actual usage test by 10 professional panelists was performed for the presence or absence of a sticky feeling after the use of the sample. The evaluation criteria were as follows.

⊚: 8 or more panelists acknowledged that there was no sticky feeling after use.

O: 6 or more and less than 8 panelists acknowledged that there was no sticky feeling after use.

Δ: 3 or more and less than 6 panelists acknowledged that there was no sticky feeling after use.

X: less than 3 panelists acknowledged that there was no sticky feeling after use.

Evaluation (3): Evaluation of Refreshing Feeling Upon Application

The actual usage test of each sample was performed by 10 professional panelists. The evaluation criteria were as follows.

⊚: 8 or more panelists acknowledged a refreshing feeling upon application.

O: 6 or more and less than 8 panelists acknowledged a refreshing feeling upon application.

Δ: 3 or more and less than 6 panelists acknowledged a refreshing feeling upon application.

X: less than 3 panelists acknowledged a refreshing feeling upon application.

Makeup compositions having the blending compositions listed in Table 14 were produced, and the above-described evaluations (1) to (3) were performed for each sample.

TABLE 14

|  | Test Example | | | | |
| --- | --- | --- | --- | --- | --- |
|  | 53 | 54 | 55 | 56 | 57 |
| (Phase A) | | | | | |
| Ion-exchanged water | Balance | Balance | Balance | Balance | Balance |
| Dimethyl distearyl ammonium chloride | — | 0.03 | 0.03 | — | — |
| Silica-coated titanium dioxide (10 nm) | 5.0 | — | 5.0 | — | — |
| 1,3-butylene glycol | 5.0 | 5.0 | 5.0 | 5.0 | 5.0 |
| Succinoglycan | 0.3 | 0.3 | 0.3 | 0.3 | 0.3 |
| Methyl paraben | 0.1 | 0.1 | 0.1 | 0.1 | 0.1 |
| PEG-60 hydrogenated castor oil | — | — | — | 2.0 | — |
| PEG-11 methyl ether dimethicone | — | — | — | — | 2.0 |
| (Phase B) | | | | | |
| Decamethylcyclopentasiloxane | 15.0 | 15.0 | 15.0 | 15.0 | 15.0 |
| Dimethylpolysiloxane 6cs | 5.0 | 5.0 | 5.0 | 5.0 | 5.0 |
| Isostearic acid | 0.5 | 0.5 | 0.5 | 0.5 | 0.5 |
| Biterminally silicone-modified glycerin represented by Formula (II) | 3.0 | 3.0 | 3.0 | 3.0 | 3.0 |
| Akyl-modified silicone resin-coated titanium oxide | 6.0 | 6.0 | 6.0 | 6.0 | 6.0 |
| Akyl-modified silicone resin-coated red iron oxide | 0.5 | 0.5 | 0.5 | 0.5 | 0.5 |
| Akyl-modified silicone resin-coated yellow iron oxide | 1.3 | 1.3 | 1.3 | 1.3 | 1.3 |
| Akyl-modified silicone resin-coated black iron oxide | 0.2 | 0.2 | 0.2 | 0.2 | 0.2 |
| PEG-10 dimethicone | 0.5 | 0.5 | 0.5 | 0.5 | 0.5 |
| Evaluation (1) Formulation stability | X | X | ○ | Δ | ○ |
| Evaluation (2) Sticky feeling | ○ | Δ | ◎ | X | X |
| Evaluation (3) Refreshing feeling | ◎ | ◎ | ◎ | X | X |

(Production Method)

Phase A was heated to 70° C. and dispersed by ultrasonic wave treatment. Phase B was added to this, the mixture was emulsified with an emulsifying machine, and then it was cooled.

As shown in Table 14, in Test Example 53, wherein a cationic surfactant was not contained and only a hydrophilic powder was blended, and in Test Example 54, wherein only a cationic surfactant was blended, the emulsification was significantly poor. In contrast, in Test Example 55, wherein both a cationic surfactant and a hydrophilic powder were blended, the formulation stability, non-stickiness, and a refreshing feeling were all good.

The composition of Test Example 56, wherein a hydrocarbon-based surfactant was used for emulsification, had poor formulation stability, a sticky feeling was present, and a refreshing feeling was absent. In Test Example 57, wherein a silicone surfactant was used, the formulation stability improved compared with the case of hydrocarbon-based surfactant. However, it was still poor in the sticky feeling and refreshing feeling.

From the above results, it was found that the excellent emulsion stability could be provided to the makeup composition of the present invention by including an oil-in-water emulsion composition containing (a) a powder component, (b) a cationic surfactant having two alkyl chains with 12 or more and 22 or less carbon atoms, (c) an oil phase component, and (d) a water phase component. In addition, the frictional feeling after use and the sticky feeling during application can be improved by blending a hydrophobized powder in the oil phase component.

The following was investigated concerning the oil phase components of the makeup composition of the present invention.

That is, makeup compositions having the blending compositions listed in Table 15 were produced, and the above-described evaluations (2) and (3) were performed for each sample.

TABLE 15

|  | Test Example | | | | |
| --- | --- | --- | --- | --- | --- |
|  | 58 | 59 | 60 | 61 | 62 |
| (Phase A) | | | | | |
| Ion-exchanged water | Balance | Balance | Balance | Balance | Balance |
| Dimethyl distearyl ammonium chloride | 0.03 | 0.03 | 0.03 | 0.03 | 0.03 |
| Silica-coated titanium dioxide (10 nm) | 5.0 | 5.0 | 5.0 | 5.0 | 5.0 |
| 1,3-butylene glycol | 5.0 | 5.0 | 5.0 | 5.0 | 5.0 |
| Succinoglycan | 0.3 | 0.3 | 0.3 | 0.3 | 0.3 |
| Methyl paraben | 0.1 | 0.1 | 0.1 | 0.1 | 0.1 |
| (Phase B) | | | | | |
| Decamethylcyclopentasiloxane | 15.0 | 15.0 | 15.0 | 18.0 | 0.5 |
| Dimethylpolysiloxane 6cs | 5.0 | 5.0 | 5.0 | 5.0 | 5.0 |
| Isostearic acid | 0.5 | 0.5 | 0.5 | 0.5 | 15.0 |

TABLE 15-continued

|  | Test Example | | | | |
| --- | --- | --- | --- | --- | --- |
|  | 58 | 59 | 60 | 61 | 62 |
| Acrylic silicone represented by Formula (I) (R is a 2-hexyl group) | 3.0 | — | 1.5 | — | 1.5 |
| Biterminally silicone-modified glycerin represented by Formula (II) | — | 3.0 | 1.5 | — | 1.5 |
| Akyl-modified silicone resin-coated titanium oxide | 6.0 | 6.0 | 6.0 | 6.0 | 6.0 |
| Akyl-modified silicone resin-coated red iron oxide | 0.5 | 0.5 | 0.5 | 0.5 | 0.5 |
| Akyl-modified silicone resin-coated yellow iron oxide | 1.3 | 1.3 | 1.3 | 1.3 | 1.3 |
| Akyl-modified silicone resin-coated black iron oxide | 0.2 | 0.2 | 0.2 | 0.2 | 0.2 |
| PEG-10 dimethicone | 0.5 | 0.5 | 0.5 | 0.5 | 0.5 |
| Evaluation (2) Sticky feeling | ◎ | ◎ | ◎ | ○ | X |
| Evaluation (3) Refreshing feeling | ◎ | ◎ | ◎ | ○ | X |

(Production Method)

Phase A was heated to 70° C. and dispersed by ultrasonic wave treatment. Phase B was added to this, the mixture was emulsified with an emulsifying machine, and then it was cooled.

As shown in Table 15, the compositions of Test Examples 58 to 61, wherein 50 mass % or higher silicone oil, with respect to the oil phase component, is contained in the oil phase, showed no sticky feeling, and a refreshing texture was present. In particular, when an acrylic silicone with a specific structure (Test Example 58) or a biterminally silicone-modified glycerin (Test Example 59) was blended, or when both of them were blended (Test Example 60), a significant improvement in usability was observed. On the other hand, in Test Example 62, wherein the blending quantity of a silicone oil is less than 50 mass % with respect to the oil phase component, the sample was extremely sticky, and a refreshing feeling was also absent.

From the above results, it is preferable that 50 mass % or higher silicone oil, with respect to the oil phase component, is contained in the makeup composition of the present invention. It is clear that the blending of an acrylic silicone with a specific structure and/or biterminally silicone-modified glycerin is especially preferable for the improvement of usability.

Subsequently, in order to investigate the preferable blending quantity of the powder used in emulsification, makeup compositions having the blending compositions listed in Table 16 were produced, and the above-described evaluation tests (1) to (3) were performed for each sample.

TABLE 16

|  | Test Example | | | | |
| --- | --- | --- | --- | --- | --- |
|  | 63 | 64 | 65 | 66 | 67 |
| (Phase A) | | | | | |
| Ion-exchanged water | Balance | Balance | Balance | Balance | Balance |
| Dimethyl distearyl ammonium chloride | 0.03 | 0.03 | 0.03 | 0.03 | 0.03 |
| Silica-coated zinc oxide (30 nm) | 0.5 | 1.0 | 5.0 | 20.0 | 30.0 |
| 1,3-butylene glycol | 5.0 | 5.0 | 5.0 | 5.0 | 5.0 |
| Succinoglycan | 0.3 | 0.3 | 0.3 | 0.3 | 0.3 |
| Methyl paraben | 0.1 | 0.1 | 0.1 | 0.1 | 0.1 |
| (Phase B) | | | | | |
| Decamethylcyclopentasiloxane | 15.0 | 15.0 | 15.0 | 18.0 | 0.5 |
| Dimethylpolysiloxane 6cs | 5.0 | 5.0 | 5.0 | 5.0 | 5.0 |
| Isostearic acid | 0.5 | 0.5 | 0.5 | 0.5 | 15.0 |
| Acrylic silicone represented by Formula (I) (R is a 2-hexyl group) | 3.0 | — | 1.5 | — | 1.5 |
| Biterminally silicone-modified glycerin represented by Formula (II) | — | 3.0 | 1.5 | — | 1.5 |
| Akyl-modified silicone resin-coated titanium oxide | 6.0 | 6.0 | 6.0 | 6.0 | 6.0 |
| Akyl-modified silicone resin-coated red iron oxide | 0.5 | 0.5 | 0.5 | 0.5 | 0.5 |
| Akyl-modified silicone resin-coated yellow iron oxide | 1.3 | 1.3 | 1.3 | 1.3 | 1.3 |
| Akyl-modified silicone resin-coated black iron oxide | 0.2 | 0.2 | 0.2 | 0.2 | 0.2 |
| PEG-10 dimethicone | 0.5 | 0.5 | 0.5 | 0.5 | 0.5 |
| Evaluation (1) Formulation stability | X | ○ | ○ | ○ | Δ |
| Evaluation (2) Sticky feeling | ◎ | ◎ | ◎ | ○ | X |
| Evaluation (3) Refreshing feeling | ◎ | ◎ | ◎ | ○ | X |

(Production Method)

Phase A was heated to 70° C. and dispersed by ultrasonic wave treatment. Phase B was added to this, the mixture was emulsified with an emulsifying machine, and then it was cooled.

As shown in Table 16, the makeup compositions of Test Examples 64 to 66 had excellent formulation stability, and the non-stickiness and the refreshing feeling were also excellent. On the other hand, in Test Example 63, wherein the blending quantity of the powder component (silica-coated zinc oxide) involved in emulsification was 0.5 mass %, the formulation stability was poor. The composition in Example 67, wherein 30 mass % of the same powder component was blended, had high stickiness, and the refreshing feeling was absent.

Accordingly, in the makeup composition of the present invention, it is preferable that the blending quantity of the powder component is 1 to 20 mass % with respect to the composition.

Subsequently, in order to investigate the preferable blending quantity of the cationic surfactant having two long-chain alkyl groups, makeup compositions having the blending compositions listed in Table 17 were produced, and the above-described evaluation tests (1) to (3) were performed for each sample.

(Production Method)

Phase A was heated to 70° C. and dispersed by ultrasonic wave treatment. Phase B was added to this, the mixture was emulsified with an emulsifying machine, and then it was cooled.

As shown in Table 17, the makeup compositions of Test Examples 69 to 71 had excellent formulation stability, and the non-stickiness and the refreshing feeling were excellent. On the other hand, in Example 68, wherein the blending quantity of dimethyl distearyl ammonium chloride was 0.0005 mass %, and in Test Example 72, wherein the blending quantity was 1 mass %, the formulation stability was significantly low.

Accordingly, in the makeup composition of the present invention, it is preferable to blend 0.001 to 0.5 mass %, with respect to the composition, of the cationic surfactant having two alkyl chains with 12 or more and 22 or less carbon atoms.

Subsequently, makeup compositions having the blending compositions listed in Table 18 were produced, and the above-described evaluation tests (1) to (3) were performed for each sample.

TABLE 17

|  | Test Example | | | | |
|---|---|---|---|---|---|
|  | 68 | 69 | 70 | 71 | 72 |
| (Phase A) | | | | | |
| Ion-exchanged water | Balance | Balance | Balance | Balance | Balance |
| Dimethyl distearyl ammonium chloride | 0.0005 | 0.001 | 0.05 | 0.5 | 1.0 |
| Silica-coated zinc oxide (30 nm) | 0.5 | 1.0 | 5.0 | 20.0 | 30.0 |
| 1,3-butylene glycol | 5.0 | 5.0 | 5.0 | 5.0 | 5.0 |
| Succinoglycan | 0.3 | 0.3 | 0.3 | 0.3 | 0.3 |
| Methyl paraben | 0.1 | 0.1 | 0.1 | 0.1 | 0.1 |
| (Phase B) | | | | | |
| Decamethylcyclopentasiloxane | 15.0 | 15.0 | 15.0 | 18.0 | 0.5 |
| Dimethylpolysiloxane 6cs | 5.0 | 5.0 | 5.0 | 5.0 | 5.0 |
| Isostearic acid | 0.5 | 0.5 | 0.5 | 0.5 | 15.0 |
| Acrylic silicone represented by Formula (I) (R is a 2-hexyl group) | 3.0 | — | 1.5 | — | 1.5 |
| Biterminally silicone-modified glycerin represented by Formula (II) | — | 3.0 | 1.5 | — | 1.5 |
| Akyl-modified silicone resin-coated titanium oxide | 6.0 | 6.0 | 6.0 | 6.0 | 6.0 |
| Akyl-modified silicone resin-coated red iron oxide | 0.5 | 0.5 | 0.5 | 0.5 | 0.5 |
| Akyl-modified silicone resin-coated yellow iron oxide | 1.3 | 1.3 | 1.3 | 1.3 | 1.3 |
| Akyl-modified silicone resin-coated black iron oxide | 0.2 | 0.2 | 0.2 | 0.2 | 0.2 |
| PEG-10 dimethicone | 0.5 | 0.5 | 0.5 | 0.5 | 0.5 |
| Evaluation (1) Formulation stability | X | Δ | ◯ | ◯ | X |
| Evaluation (2) Sticky feeling | ◎ | ◎ | ◎ | ◯ | X |
| Evaluation (3) Refreshing feeling | ◎ | ◎ | ◎ | ◎ | Δ |

TABLE 18

|  | Test Example | | | |
|---|---|---|---|---|
|  | 73 | 74 | 75 | 76 |
| (Phase A) | | | | |
| Ion-exchanged water | Balance | Balance | Balance | Balance |
| Dimethyl dialkyl (C10) ammonium chloride | 0.05 | — | — | — |
| Dimethyl dialkyl (C12) ammonium chloride | — | 0.05 | — | — |
| Dimethyl dialkyl (C18) ammonium chloride | — | — | 0.05 | — |
| Dimethyl dialkyl (C22) ammonium chloride | — | — | — | 0.05 |
| Silica-coated zinc oxide (30 nm) | 3.0 | 3.0 | 3.0 | 3.0 |
| 1,3-butylene glycol | 5.0 | 5.0 | 5.0 | 5.0 |
| Succinoglycan | 0.3 | 0.3 | 0.3 | 0.3 |
| Methyl paraben | 0.1 | 0.1 | 0.1 | 0.1 |
| (Phase B) | | | | |
| Decamethylcyclopentasiloxane | 15.0 | 15.0 | 15.0 | 18.0 |
| Dimethylpolysiloxane 6cs | 5.0 | 5.0 | 5.0 | 5.0 |
| Isostearic acid | 0.5 | 0.5 | 0.5 | 0.5 |
| Acrylic silicone represented by Formula (I) (R is a 2-hexyl group) | 3.0 | — | 1.5 | — |
| Biterminally silicone-modified glycerin represented by Formula (II) | — | 3.0 | 1.5 | — |
| Akyl-modified silicone resin-coated titanium oxide | 6.0 | 6.0 | 6.0 | 6.0 |
| Akyl-modified silicone resin-coated red iron oxide | 0.5 | 0.5 | 0.5 | 0.5 |
| Akyl-modified silicone resin-coated yellow iron oxide | 1.3 | 1.3 | 1.3 | 1.3 |
| Akyl-modified silicone resin-coated black iron oxide | 0.2 | 0.2 | 0.2 | 0.2 |
| PEG-10 dimethicone | 0.5 | 0.5 | 0.5 | 0.5 |
| Evaluation(1) Formulation stability | X | ○ | ○ | ○ |
| Evaluation(2) Sticky feeling | — | ◎ | ◎ | Δ |
| Evaluation(3) Refreshing feeling | — | ◎ | ◎ | Δ |

(Production Method)

Phase A was heated to 70° C. and dispersed by ultrasonic wave treatment. Phase B was added to this, the mixture was emulsified with an emulsifying machine, and then it was cooled.

As shown in Table 18, the compositions of Test Examples 74 and 75 showed good results in all evaluation items. On the other hand, the composition in Example 73, wherein dimethyl distearyl ammonium chloride with an alkyl chain length of 10 was used, had significantly low formulation stability, and it was not usable. The composition in Example 76, wherein the alkyl chain length was 22, had excellent formulation stability; however, some stickiness was present, and it was unsatisfactory in the refreshing feeling.

Accordingly, in the makeup composition of the present invention, the length of two alkyl chains of the cationic surfactant is preferably 12 to 22.

In the following, formulation examples of the makeup composition of the present invention are listed. However, the present invention is not limited to these examples. All the makeup compositions obtained in the below-described formulation examples had high formulation stability, a low sticky feeling, and a refreshing feeling.

| Formulation example 1: oil-in-water emulsion foundation | |
|---|---|
| | (mass %) |
| (1) Hydrophobized titanium dioxide | 10.0 |
| (2) Hydrophobized talc | 3.0 |
| (3) Hydrophobized yellow iron oxide | 0.8 |
| (4) Hydrophobized black iron oxide | 0.15 |
| (5) Hydrophobized red iron oxide | 0.36 |
| (6) Biterminally silicone-modified glycerin represented by Formula (II) | 3.0 |
| (7) PEG-10 dimethicone | 0.5 |
| (8) Decamethylcyclopentasiloxane | 10.0 |
| (9) Squalane | 4.0 |
| (10) Di(propylene glycol) | 5.0 |
| (11) Silica (10 nm) | 3.0 |
| (12) Diethyl distearyl ammonium chrolide | 0.03 |
| (13) Purified water | Q.S. |
| (14) Xanthan gum | 0.3 |
| (15) Carboxymethylcellulose | 0.2 |
| (16) Ethanol | 2.0 |
| (17) Edetate | 0.1 |
| (18) Antiseptic | Q.S. |
| (19) PEG-60 hydrogenated castor oil | 0.01 |
| (20) Purified water | Balance |

(Production Method)

Components (10) to (13) were mixed and heated to 70° C. The mixture was sufficiently dispersed with a homomixer or by ultrasonic wave. Subsequently, oil phase components (1) to (9), which had been beforehand fragmented by dispersion with a bead mill, were added. After the emulsification was carried out with an emulsifying machine, components (14) to (20) were added. An oil-in-water emulsion foundation was obtained by dispersing them uniformly.

Formulation example 2: oil-in-water emulsion foundation

| | (mass %) |
|---|---|
| (1) Hydrophobized titanium dioxide | 10.0 |
| (2) Hydrophobized talc | 3.0 |
| (3) Hydrophobized yellow iron oxide | 0.8 |
| (4) Hydrophobized black iron oxide | 0.15 |
| (5) Hydrophobized red iron oxide | 0.36 |
| (6) Biterminally silicone-modified glycerin represented by Formula (II) | 3.0 |
| (7) PEG-10 dimethicone | 0.5 |
| (8) Decamethylcyclopentasiloxane | 15.0 |
| (9) Octyl methoxycinnamate | 5.0 |
| (10) Octocrylene | 2.0 |
| (11) Glycerin | 3.0 |
| (12) 1,3-butylene glycol | 4.0 |
| (13) Silica-coated zinc oxide (30 nm) | 5.0 |
| (14) Dimethyl distearyl ammonium chrolide | 0.05 |
| (15) Purified water | Q.S. |
| (16) Succinoglycan | 0.3 |
| (17) Carboxymethylcellulose | 0.2 |
| (18) Antiseptic | Q.S. |
| (19) PEG-100 hydrogenated castor oil | 0.03 |
| (20) Purified water | Balance |

(Production Method)

Components (11) to (15) were mixed and heated to 70° C. The mixture was sufficiently dispersed with a homomixer or by ultrasonic wave. Subsequently, oil phase components (1) to (10), which had been beforehand fragmented by dispersion with a bead mill, were gradually added to this. After the emulsification was carried out with an emulsifying machine, components (16) to (20) were added. An oil-in-water emulsion foundation was obtained by dispersing them uniformly.

Formulation example 3: oil-in-water gel foundation

| | (mass %) |
|---|---|
| (1) Hydrophobized titanium dioxide | 10.0 |
| (2) Hydrophobized yellow iron oxide | 0.8 |
| (3) Hydrophobized black iron oxide | 0.15 |
| (4) Hydrophobized red iron oxide | 0.36 |
| (5) Acrylic silicone represented by Formula (I) | 1.0 |
| (6) PEG-10 dimethicone | 0.5 |
| (7) Isostearic acid | 0.2 |
| (8) Decamethylcyclopentasiloxane | 12.0 |
| (9) Cetyl octanoate | 3.0 |
| (10) Glycerin | 3.0 |
| (11) Di(propylene glycol) | 4.0 |
| (12) Silica-coated titanium dioxide (10 nm) | 3.0 |
| (13) Dimethyl distearyl ammonium chrolide | 0.15 |
| (14) Purified water | Q.S. |
| (15) Xanthan gum | 0.2 |
| (16) Agar powder | 1.5 |
| (17) Edetate | 0.1 |
| (18) Antiseptic | Q.S. |
| (19) POE(20)behenyl alcohol | 0.01 |
| (20) Purified water | Balance |

(Production method)

Components (11) to (14) were mixed and heated to 70° C. The mixture was sufficiently dispersed with a homomixer or by ultrasonic wave. Subsequently, oil phase components (1) to (10), which had been beforehand fragmented by dispersion with a bead mill, were gradually added to this. After the emulsion was carried out with an emulsifying machine, components (15) to (20), which had been beforehand uniformly dispersed at 90° C. and then cooled, were added to obtain an oil-in-water gel foundation.

EXAMPLE 4

The following was investigated concerning the hair styling cosmetic of the present invention. In the examples, "mass %" or "%", which represents the blending quantity, indicates mass % with respect to the total amount of the composition unless otherwise noted.

Initially, the evaluation methods used in the present examples will be explained.

Evaluation (1): Emulsion Stability (Emulsified Particles)

When the sample appearance was observed with an optical microscope within 1 day after emulsion preparation, O: Emulsified particles were uniform, and the coalescence or aggregation was not observed.

Δ: Emulsified particles were nearly uniform; however, slight coalescence or aggregation was observed.

X: Emulsified particles were not uniform, and significant coalescence or aggregation was observed.

Evaluation (2): Hair Styling Power

The actual usage test by 10 professional panelists was performed for the hair styling power of the samples. The evaluation criteria were as follows.

⊚: 8 or more panelists acknowledged that the natural hair styling with natural hair flow could be maintained.

O: 6 or more and less than 8 panelists acknowledged that the natural hair styling with natural hair flow could be maintained.

Δ: 3 or more and less than 6 panelists acknowledged that the natural hair styling with natural hair flow could be maintained.

X: less than 3 panelists acknowledged that the natural hair styling with natural hair flow could be maintained.

Evaluation (3): Moisture Resistance

A sample was applied on the hair strand, and the strand was formed into coils, naturally dried, and stored for 24 hours in a container that was adjusted at a relative humidity of 90% and 25° C. The sensory evaluation, for the shape and texture of the removed strand, was performed by 10 panelists. The determination was based on the following criteria.

⊚: 8 or more panelists determined that there was moisture resistance.

O: 6 or more and less than 8 panelists determined that there was moisture resistance.

Δ: 3 or more and less than 6 panelists determined that there was moisture resistance.

X: less than 3 panelists determined that there was moisture resistance.

Evaluation (4): Evaluation of Sticky Feeling Upon Application

The actual usage test of each sample was performed by 10 professional panelists. The evaluation criteria were as follows.

⊚: 8 or more panelists acknowledged that there was no sticky feeling upon application.

O: 6 or more and less than 8 panelists acknowledged that there was no sticky feeling upon application.

Δ: 3 or more and less than 6 panelists acknowledged that there was no sticky feeling upon application.

X: less than 3 panelists acknowledged that there was no sticky feeling upon application.

Hair styling cosmetics having the blending compositions listed in Table 19 were produced, and the above-described evaluation tests (1) to (4) were performed for each sample.

TABLE 19

| | Test Example | | | |
|---|---|---|---|---|
| | 77 | 78 | 79 | 80 |
| (Phase A) | | | | |
| Ion-exchanged water | Balance | Balance | Balance | Balance |
| Dimethyl distearyl ammonium chloride | — | 0.07 | 0.07 | — |
| Silica-coated titanium dioxide (10 nm) | 4.0 | — | 4.0 | — |
| Silica (10 nm) | 1.0 | — | 1.0 | — |
| Propylene glycol | 10.0 | 10.0 | 10.0 | 10.0 |
| Succinoglycan | 0.3 | 0.3 | 0.3 | 0.3 |
| PEG-60 hydrogenated castor oil | — | — | — | 0.2 |
| (Phase B) | | | | |
| Liquid paraffin | 10.0 | 10.0 | 10.0 | 10.0 |
| Pentaerythritol tetraethylhexanoate | 3.0 | 3.0 | 3.0 | 3.0 |
| Petrolatum | 6.0 | 6.0 | 6.0 | 6.0 |

TABLE 19-continued

| | Test Example | | | |
|---|---|---|---|---|
| | 77 | 78 | 79 | 80 |
| Microcrystalline wax | 10.0 | 10.0 | 10.0 | 10.0 |
| Carnauba wax | 3.5 | 3.5 | 3.5 | 3.5 |
| Evaluation(1) Emulsion stability | X | X | ○ | Δ |
| Evaluation(2) Hair styling power | — | — | ◎ | Δ |
| Evaluation(3) Moisture resistance | — | — | ◎ | Δ |
| Evaluation(4) Sticky feeling | — | — | ◎ | X |

(Production Method)

Phase A was heated to 70° C. and dispersed by ultrasonic wave treatment. Phase B heated to 80° C. was added to this, the emulsification was carried out with an emulsifying machine, and then it was cooled.

As shown in Table 19, Test Example 77, wherein the emulsification was carried out with the use of a hydrophilic powder (silica-coated titanium dioxide, silica), and Test Example 78, wherein the emulsification was carried out with the use of dimethyl distearyl ammonium chloride, showed significantly poor emulsion stability. In contrast, Test Example 79, wherein the emulsification was carried out with the use of both dimethyl distearyl ammonium chloride and a hydrophilic powder, showed high emulsion stability, and the good usability was shown in hair styling power, moisture resistance, and non-stickiness.

In addition, the composition of Test Example 80, wherein the emulsification was carried out with the use of only PEG-60 hydrogenated castor oil, which is a hydrocarbon-based surfactant, had poor emulsion stability, and the usability was unsatisfactory.

Accordingly, it is preferable that the hair styling cosmetic of the present invention contain an oil-in-water emulsion composition containing (a) a powder component, (b) a cationic surfactant having two alkyl chains with 12 or more and 22 or less carbon atoms, (c) an oil phase component, and (d) a water phase component.

Subsequently, in order to investigate the preferable blending quantity of the powder used in emulsification, hair styling cosmetics having the blending compositions listed in Table 20 were produced, and the above-described evaluation tests (1) to (4) were performed for each sample.

TABLE 20

| | Test Example | | | | |
|---|---|---|---|---|---|
| | 81 | 82 | 83 | 84 | 85 |
| (Phase A) | | | | | |
| Ion-exchanged water | Balance | Balance | Balance | Balance | Balance |
| Dimethyl distearyl ammonium chloride | 0.07 | 0.07 | 0.07 | 0.07 | 0.07 |
| Silica-coated zinc oxide (30 nm) | 0.4 | 0.8 | 4.0 | 16.0 | 24.0 |
| Silica (10 nm) | 0.1 | 0.2 | 1.0 | 4.0 | 4.0 |
| Propylene glycol | 10.0 | 10.0 | 10.0 | 10.0 | 10.0 |
| Succinoglycan | 0.3 | 0.3 | 0.3 | 0.3 | 0.3 |
| PEG-60 hydrogenated castor oil | — | — | — | 2.0 | 2.0 |
| (Phase B) | | | | | |
| Liquid paraffin | 10.0 | 10.0 | 10.0 | 10.0 | 10.0 |
| Pentaerythritol tetraethylhexanoate | 3.0 | 3.0 | 3.0 | 3.0 | 3.0 |
| Petrolatum | 6.0 | 6.0 | 6.0 | 6.0 | 6.0 |
| Microcrystalline wax | 10.0 | 10.0 | 10.0 | 10.0 | 10.0 |
| Carnauba wax | 3.5 | 3.5 | 3.5 | 3.5 | 3.5 |
| Evaluation (1) Emulsion stability | X | ○ | ○ | ○ | Δ |
| Evaluation (2) Hair styling power | ○ | ◎ | ◎ | ○ | X |
| Evaluation (3) Moisture resistance | ○ | ◎ | ◎ | ○ | X |
| Evaluation (4) Sticky feeling | ○ | ◎ | ◎ | ○ | X |

(Production Method)

Phase A was heated to 70° C. and dispersed by ultrasonic wave treatment. Phase B heated to 80° C. was added to this, the emulsification was carried out with an emulsifying machine, and then it was cooled.

As shown in Table 20, the hair styling cosmetics of Test Examples 82 to 84 showed excellent emulsion stability, and they were also highly evaluated in hair styling power, moisture resistance, and the absence of a sticky feeling. On the other hand, Test Example 81, wherein the blending quantity of the powder component (silica-coated zinc oxide, silica) involved in emulsification was 0.5 mass %, had poor emulsion stability. The composition of Example 85, wherein 30 mass % of the powder component was blended, severely lacked usability.

Accordingly, it is preferable that the blending quantity of the powder component in the hair styling cosmetic of the present invention is 1 to 20 mass % with respect to the composition.

Subsequently, in order to investigate the preferable blending quantity of the cationic surfactant having two long-chain alkyl groups, hair styling cosmetics having the blending compositions listed in Table 21 were produced, and the above-described evaluation tests (1) to (4) were performed for each sample.

TABLE 21

| | Test Example | | | | |
|---|---|---|---|---|---|
| | 86 | 87 | 88 | 89 | 90 |
| (Phase A) | | | | | |
| Ion-exchanged water | Balance | Balance | Balance | Balance | Balance |
| Dimethyl distearyl ammonium chloride | 0.0005 | 0.001 | 0.05 | 0.5 | 1.0 |
| Silica-coated zinc oxide (30 nm) | 4.0 | 4.0 | 4.0 | 4.0 | 4.0 |
| Silica (10 nm) | 1.0 | 1.0 | 1.0 | 1.0 | 1.0 |
| Propylene glycol | 10.0 | 10.0 | 10.0 | 10.0 | 10.0 |
| Succinoglycan | 0.3 | 0.3 | 0.3 | 0.3 | 0.3 |
| PEG-60 hydrogenated castor oil | — | — | — | 2.0 | 2.0 |
| (Phase B) | | | | | |
| Liquid paraffin | 10.0 | 10.0 | 10.0 | 10.0 | 10.0 |
| Pentaerythritol tetraethylhexanoate | 3.0 | 3.0 | 3.0 | 3.0 | 3.0 |
| Petrolatum | 6.0 | 6.0 | 6.0 | 6.0 | 6.0 |
| Microcrystalline wax | 10.0 | 10.0 | 10.0 | 10.0 | 10.0 |
| Carnauba wax | 3.5 | 3.5 | 3.5 | 3.5 | 3.5 |
| Evaluation (1) Emulsion stability | X | ○ | ○ | ○ | X |
| Evaluation (2) Hair styling power | ○ | ◎ | ◎ | ○ | X |
| Evaluation (3) Moisture resistance | ○ | ◎ | ◎ | ○ | X |
| Evaluation (4) Sticky feeling | ○ | ◎ | ◎ | ◎ | X |

(Production Method)

Phase A was heated to 70° C. and dispersed by ultrasonic wave treatment. Phase B heated to 80° C. was added to this, the emulsification was carried out with an emulsifying machine, and then it was cooled.

As shown in Table 21, the hair styling cosmetics of Test Examples 87 to 89 showed high emulsion stability, and they were also excellent in hair styling power, moisture resistance, and nonsticky feeling. On the other hand, Example 86, wherein the blending quantity of dimethyl distearyl ammonium chloride was 0.0005 mass %, had low emulsion stability. Test Example 90, wherein the blending quantity was 1 mass %, had both poor emulsion stability and poor usability.

Accordingly, in the hair styling cosmetic of the present invention, it is preferable that 0.001 to 0.5 mass % of the cationic surfactant having two alkyl chains with 12 or more and 22 or less carbon atoms is blended with respect to the composition.

Subsequently, hair styling cosmetics having the blending compositions listed in Table 22 were produced, and the above-described evaluation tests (1) to (4) were performed for each sample.

TABLE 22

| | Test Example | | | |
|---|---|---|---|---|
| | 91 | 92 | 93 | 94 |
| (Phase A) | | | | |
| Ion-exchanged water | Balance | Balance | Balance | Balance |
| Dimethyl dialkyl (C10) ammonium chloride | 0.07 | — | — | — |
| Dimethyl dialkyl (C12) ammonium chloride | — | 0.07 | — | — |
| Dimethyl dialkyl (C18) ammonium chloride | — | — | 0.07 | — |
| Dimethyl dialkyl (C22) ammonium chloride | — | — | — | 0.07 |
| Silica-coated zinc oxide (30 nm) | 4.0 | 4.0 | 4.0 | 4.0 |
| Silica (10 nm) | 1.0 | 1.0 | 1.0 | 1.0 |
| Propylene glycol | 10.0 | 10.0 | 10.0 | 10.0 |
| Succinoglycan | 0.3 | 0.3 | 0.3 | 0.3 |
| (Phase B) | | | | |
| Liquid paraffin | 10.0 | 10.0 | 10.0 | 10.0 |
| Pentaerythritol tetraethylhexanoate | 3.0 | 3.0 | 3.0 | 3.0 |
| Petrolatum | 6.0 | 6.0 | 6.0 | 6.0 |
| Microcrystalline wax | 10.0 | 10.0 | 10.0 | 10.0 |
| Carnauba wax | 3.5 | 3.5 | 3.5 | 3.5 |
| Evaluation(1) Emulsion stability | X | ○ | ○ | Δ |
| Evaluation(2) Hair styling power | — | ◎ | ◎ | Δ |
| Evaluation(3) Moisture resistance | — | ◎ | ◎ | Δ |
| Evaluation(4) Sticky feeling | — | ◎ | ◎ | Δ |

(Production Method)

Phase A was heated to 70° C. and dispersed by ultrasonic wave treatment. Phase B heated to 80° C. was added to this, the emulsification was carried out with an emulsifying machine, and then it was cooled.

As shown in Table 22, the compositions of Test Examples 92 and 93 showed good results in all evaluation items. On the other hand, the composition in Example 91, wherein dimethyl distearyl ammonium chloride with an alkyl chain length of 10 was used, had significantly low emulsion stability, and it was not usable. The composition in Example 94, wherein the alkyl chain length was 22, had both unsatisfactory formulation stability and unsatisfactory usability.

Accordingly, in the hair styling cosmetic of the present invention, the length of two alkyl chains of the cationic surfactant is preferably 12 to 22.

Subsequently, in order to investigate the preferable oil components for the present invention, hair styling cosmetics having the blending compositions listed in Table 23 were produced, and the above-described evaluation tests (2) to (4) were performed for each sample.

TABLE 23

| | Test Example | | | | |
|---|---|---|---|---|---|
| | 95 | 96 | 97 | 98 | 99 |
| (Phase A) | | | | | |
| Ion-exchanged water | Balance | Balance | Balance | Balance | Balance |
| Dimethyl dialkyl (C12) ammonium chloride | 0.07 | 0.07 | 0.07 | 0.07 | 0.07 |
| Silica-coated zinc oxide (30 nm) | 4.0 | 4.0 | 4.0 | 4.0 | 4.0 |
| Silica (10 nm) | 1.0 | 1.0 | 1.0 | 1.0 | 1.0 |
| Propylene glycol | 10.0 | 10.0 | 10.0 | 10.0 | 10.0 |
| Succinoglycan | 0.3 | 0.3 | 0.3 | 0.3 | 0.3 |
| (Phase B) | | | | | |
| Liquid paraffin | — | 20.0 | 7.0 | 7.0 | 30.0 |
| Pentaerythritol tetraethylhexanoate | — | — | 3.0 | 3.0 | 10.0 |
| Microcrystalline wax | 20.0 | — | 10.0 | 40.0 | 10.0 |
| Evaluation(2) Hair styling power | Δ | X | ◎ | Δ | Δ |
| Evaluation(3) Moisture resistance | Δ | Δ | ◎ | Δ | Δ |
| Evaluation(4) Sticky feeling | X | Δ | ◎ | Δ | Δ |

(Production Method)

Phase A was heated to 70° C. and dispersed by ultrasonic wave treatment. Phase B heated to 80° C. was added to this, the emulsification was carried out with an emulsifying machine, and then it was cooled.

As shown in Table 23, in Test Example 95, wherein only solid oil was blended as the oil phase component, the sticky feeling was high. In Test Example 96, wherein only liquid oil was blended, the hair styling power was poor. In contrast, the composition of Test Example 97, wherein suitable amounts of solid oil and liquid oil were blended, showed excellent results in all items.

On the other hand, in Test Examples 98 and 99, wherein a large amount of solid oil or liquid oil was blended, the results showed poorer usability compared with Test Example 97.

Accordingly, in hair styling cosmetic of the present invention, it is preferable to blend suitable amounts of solid oil and liquid oil as the oil phase components.

As a result of further investigation, it was found that the respective blending quantities of solid oil and liquid oil were preferably 1 to 30 mass % with respect to the total components.

In the following, formulation examples of the hair styling cosmetic of the present invention are listed. However, the present invention is not limited to these examples. All the hair styling cosmetics obtained in the below-described formulations examples had high emulsion stability and a low sticky feeling, and the hair styling power and moisture resistance were excellent.

| Formulation example 1: hair wax | |
|---|---|
| | (mass %) |
| Phase A | |
| Liquid paraffin | 10.0 |
| Microcrystalline wax | 5.0 |
| Carnauba wax | 5.0 |
| Pentaerythritol tetra-2-ethylhexanoate | 3.0 |
| Phase B | |
| 1,3-butylene glycol | 7.0 |
| Silica-coated zinc oxide (30 nm) | 3.0 |
| Diethyl distearyl ammonium chloride | 0.03 |
| Silica (10 nm) | 1.0 |
| Purified water | Q.S. |
| Phase C | |
| Triethanolamine | 0.3 |
| Ethanol | 2.0 |
| Carboxyvinyl polymer | 0.2 |
| Paraoxybenzoic acid ester | Q.S. |
| Trisodium edetate | Q.S. |
| PEG-100 hydrogenated castor oil | 0.05 |
| Purified water | Balance |

(Production Method)

Phase B was heated to 70° C. and dispersed by ultrasonic wave treatment. Phase A heated to 80° C. was added to this, the emulsification was carried out with an emulsifying machine, phase C was added, and then it was cooled.

| Formulation example 2: hair wax | |
|---|---|
| | (mass %) |
| Phase A | |
| Liquid paraffin | 10.0 |
| Microcrystalline wax | 10.0 |
| Dimethylpolysiloxane | 4.0 |
| Stearyl alcohol | 2.0 |
| Carnauba wax | 3.0 |
| Pentaerythritol tetra-2-ethylhexanoate | 2.0 |
| Perfume | Q.S. |
| Phase B | |
| Propylene glycol | 8.0 |
| Silica-coated zinc oxide (30 nm) | 2.0 |
| Diethyl distearyl ammonium chloride | 0.07 |
| Silica (10 nm) | 2.0 |
| Purified water | Q.S. |
| Phase C | |
| Succinoglycan | 0.2 |
| Glycerin | 3.0 |
| L-Arginine L-aspartate | 0.01 |
| Edetate | 0.05 |
| Antiseptic | Q.S. |
| POE(20)behenyl alcohol | 0.02 |
| Purified water | Balance |

(Production Method)

Phase B was heated to 70° C. and dispersed by ultrasonic wave treatment. Phase A heated to 80° C. was added to this, the emulsification was carried out with an emulsifying machine, phase C was added, and then it was cooled.

What is claimed is:

1. An oil-in-water emulsion composition comprising
   (a) 1 to 10 mass % of a powder component comprising powder particles,
   (b) 0.001 to 0.5 mass % of dimethyl dialkl ammonium chloride having two alkyl chains each with 12 to 22 carbon atoms,
   (c) an oil phase component, and
   (d) a water phase component, wherein the oil phase component takes the form of oil droplets dispersed in the water phase component,
wherein the (a) powder particles are adsorbed on the oil droplets dispersed in the water phase, and
wherein the (b) dimethyl dialkyl ammonium chloride is adsorbed on the (a) powder particles.

2. The oil-in-water emulsion composition of claim 1, wherein the total amount of the (b) dimethyl dialkl ammonium chloride is 0.001 to 0.1 mass %.

3. The oil-in-water emulsion composition of claim 1, wherein the (d) water phase component further comprises one or more selected from the group consisting of succinoglycan, xanthan gum, and acrylamide.

4. The oil-in-water emulsion composition of claim 1, wherein the water phase further comprises 0.001 to 0.5 mass % of a hydrophilic surfactant.

5. The oil-in-water emulsion composition of claim 2, wherein the (d) water phase component comprises one or more selected from the group consisting of succinoglycan, xanthan gum, and acrylamide.

6. An external skin preparation for sunscreen comprising:
an oil-in-water emulsion composition comprising:
  (a) 1 to 10 mass % of a powder component comprising powder particles,
  (b) 0.001 to 0.5 mass % of dimethyl dialkyl ammonium chloride having two alkyl chains each with 12 to 22 carbon atoms,
  (c) an oil phase component, and
  (d) a water phase component, wherein the oil phase component takes the form of oil droplets dispersed in the water phase component, the (a) powder particles are adsorbed on the oil droplets dispersed in the water phase, and the (b) dimethyl dialkyl ammonium chloride is adsorbed on the (a) powder particles; and
a hydrophobized powder dispersed in the (c) oil phase component.

7. The preparation of claim 6, wherein the hydrophobized powder comprises at least one of hydrophobized titanium dioxide fine particles and hydrophobized zinc oxide fine particles.

8. A makeup composition comprising:
an oil-in-water emulsion composition comprising:
  (a) 1 to 10 mass % of a powder component comprising powder particles,
  (b) 0.001 to 0.5 mass % of dimethyl dialkyl ammonium chloride having two alkyl chains each with 12 to 22 carbon atoms,
  (c) an oil phase component, and
  (d) water phase component, wherein the oil abase component takes the form of oil droplets dispersed in the water phase component, the (a) powder particles are adsorbed on the oil droplets dispersed in the water phase, and the (b) dimethyl dialkyl ammonium chloride is adsorbed on the (a) powder particles; and
a hydrophobized powder dispersed in the (c) oil phase component,
wherein 50 mass % or more of the oil phase component is a silicone oil.

9. The makeup composition according to the claim 8, wherein the hydrophobized powder comprises the hydrophobized fine particles of one or more selected from the group consisting of titanium dioxide, red iron oxide, yellow iron oxide, black iron oxide, and aluminum oxide.

10. The makeup composition of claim 8 comprising one or more acrylic silicones represented by the below-described general formula (I):

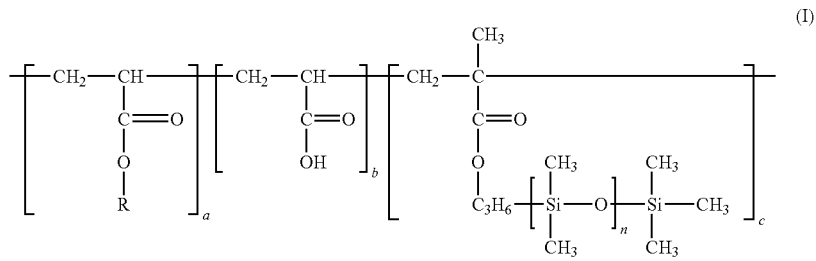

wherein R is an alkyl group having 10 to 20 carbon atoms, a+b+c=1, all of a, b, c are 0.2 or higher, and d is an integer of 5 to 100.

11. The makeup composition of claim 8, comprising one or more biterminaliy silicone-modified glycerins represented by the below-described general formula (II):

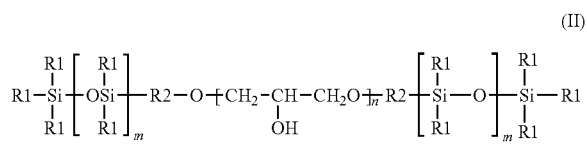

wherein R1 is a linear or branched alkyl group having 1 to 12 carbon atoms or a phenyl group, R2 is an alkylene group having 2 to 11 carbon atoms, m is 10 to 120, and n is 1 to 11.

12. A hair styling cosmetic comprising:
an oil-in-water emulsion composition comprising:
  (a) 1 to 10 mass %of a powder component comprising powder particles,
  (b) 0.001 to 0.5 mass % of dimethyl dialkyl ammonium chloride having two alkyl chains each with 12 to 22 carbon atoms,
  (c) an oil phase component, and
  (d) a water phase component, wherein the oil phase component takes the form of oil droplets dispersed in the water phase component, the (a) powder particles are adsorbed on the oil droplets dispersed in the water phase, the (b) dimethyl dialkyl ammonium chloride is adsorbed on the (a) powder particles, and the (c) oil phase component in the oil-in-water emulsion composition comprises 1 to 30 mass % of solid oil and 1 to 30 mass % of liquid oil.

13. The hair styling cosmetic according to the claim 12, wherein the (a) powder component comprises silica.

14. A method of producing the oil-in-water emulsion composition of claim 1, comprising
    (A) dispersing the powder component and the dimethyl dialkl ammonium chloride in the water phase component to form a dispersion, and
    (B) mixing the dispersion formed in (A) with the oil phase component to form the emulsion.

15. The method of claim 14, further comprising
    (C) adding and mixing a hydrophilic surfactant to the emulsion formed in (B).

16. A method of producing the oil-in-water emulsion composition of claim 2, comprising
    (A) dispersing the powder component and the dimethyl dialkl ammonium chloride in the water phase component to form a dispersion, and
    (B) mixing the dispersion formed in (A) with the oil phase component to form the emulsion.

* * * * *